US010987449B2

(12) United States Patent
Sierad et al.

(10) Patent No.: US 10,987,449 B2
(45) Date of Patent: Apr. 27, 2021

(54) DECELLULARIZATION METHOD AND SYSTEM AND DECELLULARIZED TISSUE FORMED THEREBY

(71) Applicant: CLEMSON UNIVERSITY RESEARCH FOUNDATION, Clemson, SC (US)

(72) Inventors: Leslie Sierad, Central, SC (US); Eliza Laine Shaw, Georgetown, SC (US); George Fercana, Florence, SC (US); Dan Simionescu, Pendleton, SC (US)

(73) Assignee: Clemson University Research Foundation, Clemson, SC (US)

( * ) Notice: Subject to any disclaimer, the term of this patent is extended or adjusted under 35 U.S.C. 154(b) by 98 days.

(21) Appl. No.: 16/379,121

(22) Filed: Apr. 9, 2019

(65) Prior Publication Data

US 2019/0231930 A1    Aug. 1, 2019

Related U.S. Application Data

(62) Division of application No. 14/806,824, filed on Jul. 23, 2015, now Pat. No. 10,293,082.

(60) Provisional application No. 62/028,046, filed on Jul. 23, 2014.

(51) Int. Cl.
*A61L 27/36* (2006.01)
*A61F 2/24* (2006.01)

(52) U.S. Cl.
CPC ....... *A61L 27/3687* (2013.01); *A61L 27/3604* (2013.01); *A61L 27/3625* (2013.01); *A61L 27/3691* (2013.01); *A61F 2/2415* (2013.01); *A61L 2430/20* (2013.01); *A61L 2430/40* (2013.01)

(58) Field of Classification Search
CPC ..... A61F 2/2415; A61L 27/3683–3695; A61L 2430/40
See application file for complete search history.

(56) References Cited

U.S. PATENT DOCUMENTS

| | | | |
|---|---|---|---|
| 5,846,828 A | 12/1998 | Peterson et al. |
| 5,899,937 A | 5/1999 | Goldstein et al. |
| 6,121,042 A | 9/2000 | Peterson et al. |
| 6,126,007 A | 10/2000 | Kari et al. |
| 6,132,473 A | 10/2000 | Williams et al. |

(Continued)

FOREIGN PATENT DOCUMENTS

WO    WO 2005/118014    12/2005

OTHER PUBLICATIONS

Aleksieva, et al. "Use fo a special bioreactor for the cultivation of a new flexible polyurethane scaffold for aortic valve tissue engineering" *BioMedical Engineering OnLine* 11(1):92 (2012) pp. 1-11.

(Continued)

*Primary Examiner* — Thaddeus B Cox
(74) *Attorney, Agent, or Firm* — Dority & Manning, P.A.

(57) ABSTRACT

Systems and methods that establish a pressure differential across a tissue wall to encourage complete decellularization of the wall are described. The methods can be utilized for decellularization of blood vessel tissue including heart valves and surrounding tissues. The methods and systems can essentially completely decellularize the treated tissue segments. Systems can be utilized to decellularize one or multiple tissue segments at a single time.

16 Claims, 11 Drawing Sheets

(56) References Cited

U.S. PATENT DOCUMENTS

| | | | |
|---|---|---|---|
| 6,383,732 B1 | 5/2002 | Stone |
| 6,409,758 B2 | 6/2002 | Stobie et al. |
| 6,432,712 B1 | 8/2002 | Woltmbarger, Jr. |
| 6,652,583 B2 | 11/2003 | Hopkins et al. |
| 6,702,852 B2 | 3/2004 | Stobie et al. |
| 6,881,569 B2 | 4/2005 | Perry et al. |
| 6,952,814 B2 | 10/2005 | Joseph et al. |
| 6,964,682 B2 | 11/2005 | Nguyen-Thien-Nhon et al. |
| 6,966,925 B2 | 11/2005 | Stobie |
| 7,063,942 B2 | 6/2006 | Dancu et al. |
| 7,112,218 B2 | 9/2006 | McAllister et al. |
| 7,179,287 B2 | 2/2007 | Wolfinbarger, Jr. |
| 7,252,834 B2 | 8/2007 | Vyavahare et al. |
| 7,378,271 B2 | 5/2008 | Bader |
| 7,439,057 B2 | 10/2008 | Frangos et al. |
| 7,498,412 B2 | 3/2009 | Huang et al. |
| 7,504,258 B2 | 3/2009 | McAllister et al. |
| 7,645,568 B2 | 1/2010 | Stone |
| 7,658,763 B2 | 2/2010 | Stobie |
| 7,691,046 B2 | 4/2010 | Sullivan |
| 7,744,526 B2 | 6/2010 | McAllister et al. |
| 7,753,840 B2 | 7/2010 | Simionescu et al. |
| 7,754,232 B2 | 7/2010 | Fisher et al. |
| 7,819,915 B2 | 10/2010 | Stobie et al. |
| 7,851,200 B2 | 12/2010 | More |
| 7,871,367 B2 | 1/2011 | Anderson et al. |
| 8,230,717 B2 | 7/2012 | Matonick |
| 8,308,629 B2 | 11/2012 | Watschke et al. |
| 8,399,243 B2 | 3/2013 | Bouten et al. |
| 8,491,457 B2 | 7/2013 | Atala et al. |
| 8,609,415 B2 | 12/2013 | Kortsmit et al. |
| 2002/0115208 A1 | 8/2002 | Mitchell et al. |
| 2004/0052830 A1 | 3/2004 | Konertz et al. |
| 2007/0260109 A1* | 11/2007 | Squillace ............ A61L 27/3687 600/36 |
| 2010/0093066 A1 | 4/2010 | Taylor et al. |
| 2011/0165676 A1 | 7/2011 | Hopkins |
| 2014/0018909 A1* | 1/2014 | Simionescu ........ A61L 27/3687 623/1.49 |
| 2014/0302480 A1 | 10/2014 | Ott |
| 2014/0302481 A1 | 10/2014 | Chin et al. |
| 2014/0377864 A1* | 12/2014 | Sumitran-Holgersson ................... A61L 27/3616 435/373 |
| 2015/0088247 A1* | 3/2015 | L'Heureux ............ A61F 2/2427 623/2.11 |
| 2015/0190548 A1 | 7/2015 | Sibbons et al. |
| 2015/0289967 A1* | 10/2015 | Grant ...................... A61L 27/32 623/13.17 |
| 2017/0072100 A1* | 3/2017 | Gilbert ................. A61L 27/3641 |

OTHER PUBLICATIONS

Baraki, et al. "Orthotopic replacement of the aortic valve with decellularized allograft in a sheep model" *Biomaterials* 30 (2009) pp. 6240-6246.

Barron, et al. "Bioreactors for Cardiovascular Cell and Tissue Growth: A Review" *Annals of Biomedical Engineering* 31 (2003) pp. 1017-1030.

Barzilla, et al. "Design and Validation of a Novel Splashing Bioreactor System for use in Mitral Valve Organ Culture" *Annals of Biomedical Engineering* 38(11) (2010) pp. 3272-3279.

Berry, et al. "Bioreactors for Development of Tissue Engineered Heart Valves" *Annals of Biomedical Engineering* 38(11) (2010) pp. 3272-3279.

Bilodeau, et al. "Bioreactors for Development Tissue Engineering: Focus on Mechanical Constraints. A Comparative Review" *Tissue Engineering* 12(8) (2006) pp. 2367-2384.

Bowles, et al. "Hydrodynamic Evaluation of a Bioreactor for Tissue Engineering Heart Valves" *Cardiovascular Engineering and Technology* 1(1) (2010) pp. 10-17.

Brazile, et al. "On the Bending Properties of Porcine Mitral, Tricuspid, Aortic, and Pulmonary Valve Leaflets" *Journal of Long-Term Effects of Medical Implants* 25(1-2) (2014) pp. 41-53.

Breuer, et al. "Application of Tissue-Engineering Principles toward the Development of a Semilunar Heart Valve Substitute" *Tissue Engineering* 10(11/12) (2004) pp. 1725-1738.

Butler, Ph.D. et al. "Using Functional Tissue Engineering and Bioreactors to Mechanically Stimulate 2 Tissue-Engineered Constructs" *Tissue Engineering Part A* 15(4) (2009) pp. 741-751.

Caudle, N. "The Matrix Reloaded" *Glimpse* (2014) pp. 13-23.

Chow, et al. "Mitigation of diabetes-related complications in implanted collagen and elastin scaffolds using matrix-binding polyphenol" *Biomaterials* 34(3) (2013) pp. 685-695.

Colazzo, et al. "Extracellular matrix production by adipose-derived stem cells: Implications for heart valve tissue engineering" *Biomaterials* 32(1) (2011) pp. 119-127.

Deborde, et al. "Development of a Tissue Engineered Mitral Valve Scaffold" *ISACB Presentation* (2014).

Durst, et al. "Design and Physical Characterization of a Synchronous Multivalve Aortic Valve Culture System" *Annals of Biomedical Engineering* 38(2) (2010) pp. 319-325.

Elman, et al. "A comparison of adipose and bone marrow-derived mesenchymal stromal cell secreted factors in the treatment of systemic inflammation" *Journal of Inflammation* 11(1) (2014) pp. 1-8.

Engelmayr, et al. "A Novel Flex-Stretch-Flow Bioreactor for the Study of Engineered Heart Valve 2 Tissue Mechanobiology" *Annals of Biomedical Engineering* (36)(5) (2008) pp. 700-712.

Flanagan, et al. "The in vitro development of autologous fibrin-based tissue-engineered heart valves through optimized dynamic conditioning" *Biomaterials* 28 (2007) pp. 3388-3397.

Geeslin, et al. "Bioreactor for the reconstitution of a decellularized vascular matrix of biological origin" *Journal Biomedical Science and Engineering* 4 (2011) pp. 435-442.

Gheenwala, et al. "Design and Mechanical Evaluation of a Physiological Mitral Valve Organ Culture System" *Cardiovascular Engineering and Technology* 1(2) (2010) pp. 123-131.

Goldstein, et al. "Functional Tissue Engineering Requires Bioreactor Strategies" *Tissie Engineering: Part A* 15(4) (2009) pp. 739-740.

Grande-Allen, et al. "The heterogeneous biomechanics and mechanobiology of the mitral valve: implications for tissue engineering" *Curr. Cardiol. Reports* 13(2) (2011) pp. 113-120.

Hildebrand, et al. "Design and Hydrodynamic Evaluation of a Novel Pulsatile Bioreactor for Biologically Active Heart Valves" *Annals of Biomedical Engineering* 32(8) (2004) pp. 1039-1049.

Hidebrand, D. "Design and Evaluation of a Novel Pulsatile Bioreactor for Biologically Active Heart Valves" *University of Pittsburgh* (2003) pp. 1-187.

Hoerstrup, et al. "Tissue engineering of small caliber vascular grafts" *European Journal of Cardio-thoracic Surgery* 20 (2001) pp. 164-169.

Hoerstrup, et al. "Functional Living Trileafiet Heart Valves Grown In Vitro" *Circulation* 102 (Suppl III) (2000) pp. III44-III49.

Kaasi, et al. "Using a VAD-Based Bioreactor to Host a Tissue Engineered Heart Valve" *21° Congresso Brasileiro de Engenharia Biomédica* (2008) pp. 217-220.

Karim, et al. "The Cardiovascular Tissue-Reactor: A Novel Device for the Engineering of Heart Valves" *Artificial Organs* 30(10) (2006) pp. 809-814.

Kennamer, A. "Interstitial Cell Seeding and Dynamic Conchtioning of Aortic Heart Valve Scaffolds" *Clemson University* (2013) pp. 1-77.

Konduri, et al. "Normal Physiological Conditions Maintain the Biological Characteristics of Porcine Aortic Heart Valves: An Ex Vivo Organ Culture Study" *Annals of Biomedical Engineering* 33(9) (2005) pp. 1158-1166.

Lee, et al. "Endothetialization of Heart Valve Matrix Using a Computer-Assisted Pulsatile Bioreactor" *Tissue Engineering: Part A* 15(4) (2009) pp. 807-814.

Leo, et al. "Fluid Dynamic Assessment of Three Polymeric Heart Valves Using Particle Image Velocimetry" *Annals of Biomedical Engineering* 34(6) (2006) pp. 936-952.

(56) References Cited

OTHER PUBLICATIONS

Leo, et al. "A Comparison of Flow Field Structures of Two Tri-Leaflet Polymeric Heart Valves" *Annals of Biomedical Engineering* 33(4) (2005) pp. 429-443.
Liao, et al. "Effects of decellularization on mechanical and structural properties of the porcine aortic valve leaflets" *Biomaterials* 29(8) (2008) pp. 1065-1074.
Lichtenberg, et al. "In vitro re-endothelialization of detergent decellularized heart valves under simluated physiological dynamic conditions" *Biomaterials* 27 (2006) pp. 4221-4229.
Lieber, et al. "Design of a Miniature Tissue Culture System to Culture Mouse Heart Valves" *Annals of Biomedical Engineering* 38(3) (2010) pp. 674-682.
Martin, et al. "Bioreactors for tissue mass culture: Design, characterization, and recent advances" *Biomaterials* 26 (2005) pp. 7481-7503.
Martin, et al. "The role of bioreactors in tissue engineering" *Trends in Biotechnology*, 22(2) (2004) pp. 80-86.
Miller, D. "Design and Development of a Novel Bioreactor for Tissue Engineered Heart Valves" *Arizona State University* (2002) pp. 1-136.
Mol, et al. "Tissue Engineering of Human Heart Valve Leaflets: A Novel Bioreactor for a Strain-Based Conditioning Approach" *Annals of Biomedical Engineering* 33(12) (2005) pp. 1778-1788.
Montoya, et al. "Preparation of Ex Vivo-Based Biomaterials Using Convective Flow Decellularization" *Tissue Engineering: Part C* 15(2) (2009) pp. 191-193.
Morsi, et al. "Development of a novel pulsatile bioreactor for tissue culture" *J Artif Organs* 10 (2007) pp. 109-114.
Narita, et al. "Novel Pulse Duplicating Bioreactor System for Tissue-Engineered Vascular Construct" *Tissue Engineering* 10(7/8) (2004) pp. 1224-1233.
Pascal, et al. "Systems to Facilitate Adult Stem Cell Seeding of Aortic Heart Valve Scaffolds" *SCBIO* (2012).
Paz, et al. "Tissue Engineered Trachea Using Decellularizal Aorta" *J Bioengineer & Biomedical Sci* S2:001 (2011) pp. 1-7.
Ratcliffe, et al. "Bioreactors and Bioprocessing for Tissue Engineering" *Ann. N.Y. Acad. Sci.* 961 (2002) pp. 210-215.
Ruel, et al. "A New Bioreactor for the Development of Tissue-Engineered Heart Valves" *Annals of Biomedical Engineering* 37(4) (2009) pp. 674-681.
Sarkar, et al. "Addressing thrombogenicity in vascular graft construction" *Journal of Biomedical Materials Research: Part B Applied Biomaterials* 82(1) (2007) pp. 100-108. (Abstract only).
Sauer, et al. "Thoughts and Progress" *Artificial Organs* 26(8) (2002) pp. 703-733.
Schenke-Layland, et al. "Complete dynamic repopulation of decellularized heart valves by application of defined physical signals—an in vitro study" *Cardiovascular Research* 60 (2003) pp. 497-509.
Schliecher, et al., "Simplified Pulse Reactor for Real-Time Long-Term In Vitro Testing of Biological Heart Valves" *Annals Biomedical Engineering* 38(5) (2010) pp. 1919-1927.
Sierad, et al. "Bioreactor Technologies for Clinical Translation of Tissue Engineered Heart Valves" *ISACB* (2014).
Sierad, et al. "Surface Modification, Endothelial Cell Coating, and Bioreactor Testing of Mechanical Heart Valves" *Clemson University* (2013).
Sierad, et al. "Surface Modification, Endothelial Cell Coating, and Bioreactor Testing of Mechanical Heart Valves" *SBEC* (2012).
Sierad, et al. "Design and Testing of a Pulsatile Conditioning System for Dynamic Endothelialization of Polyphenol-Stabilized Tissue Engineered Heart Valves" *Cardiovascular Engineering and Technology* 1(2) (2010) pp. 138-153.
Sierad, L. "A Pulsatile Bioreactor for Conditioning Tissue Engineered Heart Valves" *Clemson University* (2009) pp. 1-95.
Simionescu, et al. "Form Follows Function: Advances in Trilayered Structure Replication for Aortic Heart Valve Tissue Engineering" *Journal of Healthcare Engineering* 3(2) (2012) pp. 179-202.
Sodian, et al. "Tissue Engineering Bioreactors: A New Combined Cell-Seeding and Perfusion System for Vascular Tissue Engineering" *Tissue Engineering* 8(5) (2002) pp. 863-870.
Sodian, et al. "New Pulsatile Bioreactor for Fabrication of Tissue-Engineered Patches" *J Biomed. Mater. Res.* 58 (2001) pp. 401-405.
Sodian, et al. "Tissue Engineering of Heart Valves: In Vitro Experiences" *Ann. Thoracic Surgery* 70 (2000) pp. 140-144.
Sodian, et al, "Tissue Engineering of a Trileafiet Heart Valve Early in Vitro Experiences with a Combined Polymer" *Tissue Engineering* 5(5) (1999) pp. 489-494.
Tedder, et al. "Stabilized Collagen Scaffolds for Heart Valve Tissue Engineering" *Tissue Engineering: Part A* 15(6) (2009) pp. 1257-1268.
Tedder, et al. "Assembly and Testing of Stem Cell-Seeded Layered Collagen Constructs for Heart Valve Tissue Engineering" *Tissue Engineering: Part A* 17(1-2) (2011) pp. 25-38.
Warnock, et al. "Design of a Sterile Organ Culture System for the Ex Vivo Study of Aortic Heart Valves" *Journal of Biomechanical Engineering* 127 (2005) pp. 857-861.
Wendt, et al. "Potential and Bottlenecks of Bioreactors in 3D Cell Culture and Tissue Manufacturing" *Advanced Materials 21* (2009) pp. 3352-3367.
Weston, et al. "Biosynthetic Activity in Heart Valve Leaflets in Response to In Vitro Flow Environments" *Annals of Biomedical Engineering* 29 (2001) pp. 752-763.
Zeltinger, et al. "Development and Characterization of Tissue-Engineered Aortic Valves" *Tissue Engineering* 7(1) (2001) pp. 9-22.
Ziegelmueller, et al. "Optical Monitoring During Bioreactor Conditioning of Tissue-Engineered Heart Valves" *Tissue Engineering* 56 (2010) pp. 228-231.
Zou, et al. "Mechanical Evaluation of Decellularized Porcine Thoracic Aorta" *Journal of Surgical Research* 175 (2012) pp. 359-368.

\* cited by examiner

DECELLULARIZATION METHOD AND SYSTEM AND DECELLULARIZED TISSUE FORMED THEREBY

CROSS REFERENCE TO RELATED APPLICATION

This application is a divisional application of U.S. patent application Ser. No. 14/806,824, having a filing date of Jul. 23, 2015, now U.S. Pat. No. 10,293,082, which claims filing benefit of U.S. Provisional Patent Application Ser. No. 62/028,046, having a filing date of Jul. 23, 2014, both of which are being incorporated herein in their entirety.

STATEMENT AS TO RIGHTS TO INVENTIONS MADE UNDER FEDERALLY SPONSORED RESEARCH

This invention was made with Government support under Grant No. RO1 HL 093399 awarded by the National Institutes of Health. The Government has certain rights in the invention.

BACKGROUND

Replacement of damaged or diseased vascular tissue has become the standard of care for much pathology. For example, the overall prevalence of heart valve disease in the United States, adjusted to the 2000 population, was estimated at that time to be 2.5%, with about 99,000 heart valve operations yearly. By 2011, it was estimated that roughly four million people in the United States were diagnosed annually with a heart valve disorder. Often, the only solution for degenerated or calcified heart valves is replacement of the entire valve, which up to now has been either a bioprosthetic or mechanical valve.

The first designs of replacement heart valves were for mechanical models, with major breakthroughs occurring in the 1950s and 1960s. The ball-in-cage design prevailed for many years until the tilting disc's emergence. The pyrolytic carbon bileaflet valve was designed in the 1970s and became the 'gold standard' for mechanical valve replacement. Since St. Jude Medical introduced the pyrolytic carbon valve, much of the innovation in this area has come to a halt and only minor features of mechanical valves have evolved over the last forty years.

Although mechanical valves are the most durable solution for heart valve replacements (typically said to last for 20-30 years), thrombogenicity of the artificial surfaces remains a cause for much concern. Not only are the devices non-biological, they also introduce turbulent flow regimes. The turbulence can activate platelets which in turn initiate the formation of thrombi. To prevent this from occurring, patients are put on life-long anticoagulant therapy that involves the administration of Warfarin. Unfortunately, because Warfarin decreases the blood's ability to coagulate on the valve, it also prevents coagulation systemically, leaving the patient vulnerable to major bleeding events. The reliance upon an expensive drug therapy and the necessity of close patient monitoring is undesirable and the main factor that has kept mechanical valve replacement out of developing countries.

A solution to the increased thrombogenicity of mechanical valves was the advent of bioprosthetic valve (BPV) technology. These valves are made from either porcine aortic valves or bovine pericardium that have been chemically fixed, cross-linking the tissue and masking the antigens present in the xenogeneic materials. BPVs are predicted to last 10-15 years, which is a lower expectation than that of mechanical valves. In addition, it has been found that after 15 years all-cause mortality is lower for patients implanted with mechanical valves as compared to BPVs. Although the mechanical valve has been shown to be more durable and can be projected to last longer, the BPV is still the best choice for those patients who cannot be put on anticoagulant regimes. In addition, certain patient populations preferably receive certain valves. For example, elderly patients (65 years and older) typically receive BPVs because of expected life span and the reduced chance for calcification, while younger patients/children receive mechanical valves due to the decreased number of expected replacements required.

More recently, tissue engineering approaches have been developed that seek to make curative solutions for patients who are seeking long-term treatment of disease and tissue degeneration. The constructs that are being researched and tested will not simply compensate for the damaged tissue; the aim is to create living tissue that can be implanted into a human that will, from that point on, grow and remodel. Ideally, a tissue engineered heart valve will resemble both the size and shape of the native valve; be durable and fully functioning with good hemodynamics; be non-immunogenic, non-inflammatory, non-thrombogenic, and non-obstructive; respond to mechanical and biological cues appropriately; grow in size with the recipient; and will adapt to changing conditions throughout the life of the recipient and valve.

Whether for study or implantation, natural and synthetic heart valve tissue (e.g., BHV and engineered tissue) is generally subjected to multiple treatment regimes. For instance, xenograft valve tissue must be decellularized to remove the native cells prior to either testing or implant. In addition, mechanical testing by use of a conditioning system can be carried out to examine and alter tissue strength or to ensure suitable strength prior to implant. Seeding of natural or synthetic scaffolds can also be carried out in development of new valves and/or to encourage integration with a recipient's natural tissue following implantation.

To be successfully utilized for implantation, natural tissue (e.g., xenographic or allographic tissue) is decellularized to remove the native cells and other immunogenic material and leave only the non-immunogenic structural materials (collagen, elastin, laminin, etc.). Typical decellularization methods include a series of chemical (e.g., detergent or enzymatic) washes that can remove the cells by immersion. Unfortunately, while typical immersion methods can completely decellularize relatively thin tissue such as the cusps of a heart valve, thicker vascular components such as the vessel walls and surrounding muscle tissue may not be completely decellularized. This can have catastrophic consequences if a patient exhibits an immunogenic reaction to the remaining cells. Even without a sudden catastrophic event, inflammation that can occur due to the remaining immunogenic materials can affect long-term success and survival of the patient.

What is needed in the art is a system and method for decellularizing tissue that can provide completely decellularized tissues, and particularly, thick tissue such as arterial walls for implantation or study.

SUMMARY

According to one embodiment, disclosed is a method for decellularizing a tissue segment that includes a lumen and a tissue wall surrounding the lumen. The tissue wall can include an interior surface that faces the lumen and an exterior surface that is opposite to the interior surface. In one embodiment, the method can be utilized to decellularize a tissue segment that includes a blood vessel and in one particular embodiment, the method can be utilized for decellularizing a heart valve root that can include a portion of the aorta and aortic sinuses.

A method can include contacting the interior surface of the tissue segment and the exterior surface of the tissue segment with decellularization solutions that can be the same as or different from each other. In addition, the method can include establishing a pressure differential across the tissue wall (i.e., from the interior surface to the exterior surface) and maintaining the pressure differential across the tissue wall for a period of time (e.g., for about 1 minute or more). In general, the pressure differential can be from about 15 mmHg (or about 2000 Pa) to about 150 mmHg (or about 20,000 Pa). The method also includes decreasing the pressure differential following the initial period of time until any remaining pressure differential across the tissue wall is about 15 mmHg (or about 2000 Pa) or less. In one embodiment, a method can also include repeating this cycle multiple times.

Also disclosed is a system for decellularizing a tissue segment that includes a lumen and a tissue wall. The system can include a decellularization chamber. The system also includes a first tissue holder that is removably attachable to a first end of the tissue segment and a second tissue holder that is removably attachable to a second end of the tissue segment. Upon attachment of a tissue segment to the first and second tissue holders and placement of the tissue segment in the decellularization chamber, a first flow path is established that passes through the lumen of the tissue segment and contacts the interior surface of the tissue wall and a second flow path is established that contacts the exterior surface the tissue wall. The system can also include a pump that can pump a decellularization solution through the first path with a pressure differential being established across the wall.

Also disclosed is a decellularized tissue segment that can be formed by use of the method and system. The decellularized tissue segment can be any excised natural tissue segment that includes a lumen and a tissue wall surrounding the lumen. The decellularized tissue segment can contain less than about 5% by weight of the cells that were present in the natural tissue segment at the time the tissue was excised.

BRIEF DESCRIPTION OF THE FIGURES

The present disclosure may be better understood with reference to the figures including.

Figure 1:
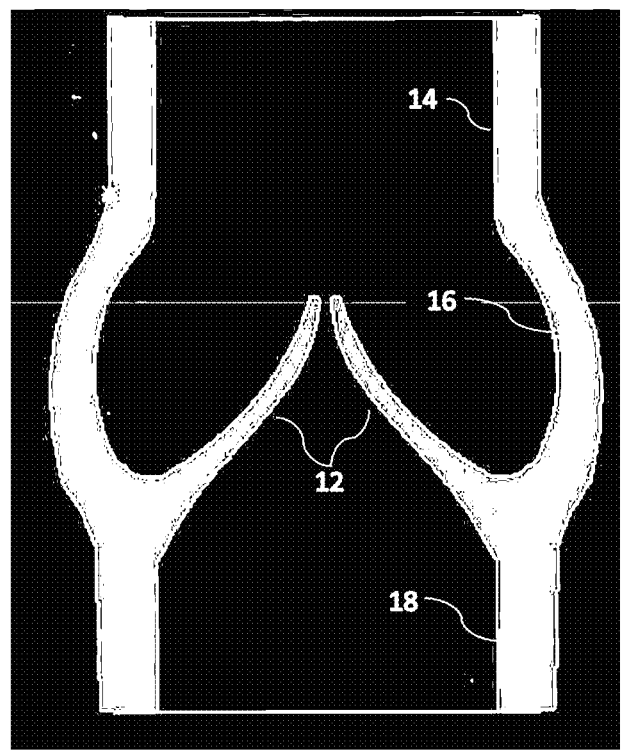
FIG. 1 is a schematic representation of a typical heart valve.

Repeat use of reference characters in the present specification and drawings is intended to represent the same or analogous features or elements of the present disclosure.

DETAILED DESCRIPTION

Reference will now be made in detail to various embodiments of the disclosure, one or more examples of which are illustrated in the accompanying drawings. Each example is provided by way of explanation of the subject matter, not limitation thereof. In fact, it will be apparent to those skilled in the art that various modifications and variations can be made in the present disclosure without departing from the scope or spirit of the subject matter. For instance, features illustrated or described as part of one embodiment, can be used on another embodiment to yield a still further embodiment.

The present disclosure relates generally to methods and systems for use in decellularizing tissue as well as to decellularized tissue that can be formed by use of the methods and systems.

As discussed above, bioprosthetic vascular implants such as BPV present many positive prospects, but serious issues still remain due to the possibility of immunogenic materials remaining in the tissues at the time of implant. FIG. 1 illustrates a generic heart valve segment including the cusps 12, vessel 14, and sinus 16 with a portion of the cardiac tissue 18 remaining. The cusps 12 are relatively thin and accessible and current standard treatment methods such as immersion in a decellularization solution are able to decellularize the cusps with high efficiency. The larger, thicker vascular components of a heart valve segment, however, presents difficulties in decellularization. For instance, an aortic wall includes the endothelium, the intima, the media and the adventitia layers, with the overall wall thickness generally from about 80 micrometers to about 4 millimeters. The multiple layers and thickness of the vessel walls 14 and sinus 16 prevent the complete decellularization of the tissue by standard immersion methods.

The disclosed systems and methods can establish a pressure differential across a tissue wall to encourage complete decellularization of the wall. While the methods can be utilized in one embodiment for decellularization of blood vessel tissue, and in one particular embodiment for decellularization of tissues surrounding and including heart valves, the disclosure is not limited to this embodiment. Beneficially, the disclosed methods and systems can be utilized to essentially completely decellularize any tissue wall that surrounds a lumen. For example, in addition to blood vessel segments, the methods and systems can be utilized to decellularize tissues of the digestive system or the urinary system as well as other tubular structures such as the trachea, the lungs, etc. In general, any tissue wall that surrounds a lumen can be decellularized according to the disclosed methods.

Figure 2:
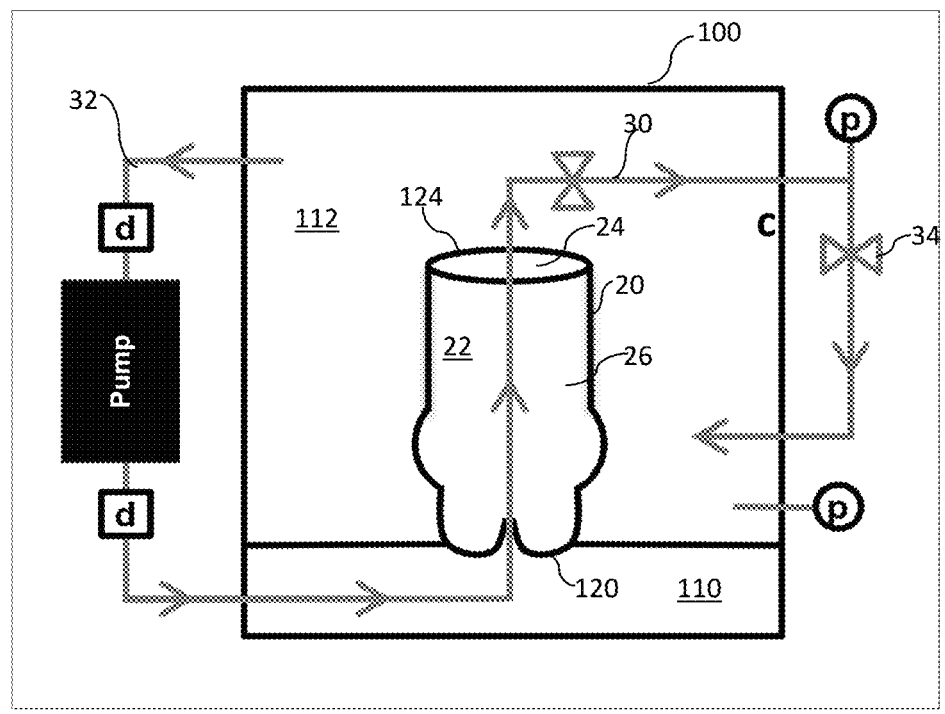
FIG. 2 schematically illustrates the disclosed method for decellularizing vascular tissue.

FIG. 2 schematically illustrates one embodiment of the decellularization method. In general, the method includes establishing a pressure differential across the wall 20 of a tissue segment 22. More specifically, the tissue segment 22 can be retained within a decellularization chamber 100 such that the lumen 24 of the tissue segment is isolated from the exterior surface 26 of the wall 20. A pressure differential can then be established across the vessel wall, i.e., from the interior surface of the tissue wall, which faces the lumen, to the exterior surface of the tissue wall, which is opposite the interior surface.

In the illustrated embodiment, the decellularization chamber 100 includes a first section 110 and a second section 112. The tissue segment 22 is held in the decellularization chamber 100 such that a first end 120 of the segment 22 is open to the first section 110. The second end 124 of the segment 22 can be held with a tissue holder (not illustrated in FIG. 2) that caps the second end 124 but allows for a flow line 30 that allows flow to exit the lumen 24 of the tissue segment 22.

A first flow path can be established via a pump. The first flow path can pass through the first section 110 of the decellularization chamber 100. This flow path can proceed through the lumen 24 of the tissue segment 22 contacting the interior surface of the tissue segment and then exit through the flow line 30.

A second flow path can pass into the second section 112 of the decellularization chamber 100. This second flow path can contact the exterior surface 22 of the tissue segment 20 and can exit the second section 112 of the decellularization chamber 100, as at 32.

In the embodiment of FIG. 2, the first flow path that passes through the flow line 30 is recycled via a valve 34 and back into the second section 112 of the decellularization chamber 100. This arrangement may prove useful as it may decrease the materials and components of a system (e.g., the number of pumps necessary), but it is not a requirement of a system, and completely separate flow paths that carry different decellularization solutions may be established, if desired. In addition, it may be beneficial to heat the fluid(s) that contact the interior and exterior portions of the tissue. When heated, the fluids can be heated to approximately body temperature, e.g., about 37° C., in one embodiment.

According to the decellularization method, a pressure differential can be established across the tissue wall 20. For instance, the fluid of the flow path within the lumen 24 can be at a higher pressure than the fluid of the flow path that contacts the exterior surface 22 of the tissue segment 20. The side of the tissue wall that sees the higher pressure is not limited, however, and the higher pressure may alternatively be on the exterior surface of the tissue segment. The pressure differential can generally be greater than about 15 mmHg (e.g., about 2000 Pa). In some embodiments, the pressure differential can be between about 15 mm Hg (about 2000 Pa) and about 150 mm Hg (about 20,000 Pa), or between about 20 mmHg (about 2500 Pa) and about 80 mmHg (about 10,500 Pa), or between about 45 mmHg (about 6000 Pa) and about 60 mmHg (about 8000 Pa).

In addition to establishing the pressure differential across the tissue wall, the method can include cyclic pulsing of the pressure differential, though this is not a requirement of a decellularization process. The pulsatile action of the flow can further encourage the decellularization of the tissue. The high pressure differential across the tissue wall can be held for a period of time that is generally about 1 minute or greater, for instance about 2 minutes or greater in some embodiments, during which pressure can be held at the desired pressure differential. If desired, flow can be stopped during this period to maintain the high pressure differential. This is not a requirement of the system, however, and flow can continue during all or a portion of the period of high pressure differential. The high pressure differential can last about 10 minutes or less, for instance about 5 minutes or less in some embodiments.

Following the period of high pressure, flow can begin again, if necessary, and the pressure can drop to a low pressure differential at which point flow can stop for a period of time to maintain the low pressure differential for the period or can continue during all or a portion of the period of low pressure differential, as desired. The low pressure differential component can establish a zero pressure differential across the tissue wall, though in other embodiments there may still be a slight pressure differential, e.g., about 15 mm Hg (about 2000 Pa) or less or about 10 mmHg (e.g., about 1300 Pa) or less in some embodiments. Flow can continue throughout the low pressure period or may stop. The period of the low pressure component can be the same as, longer than, or less than that of the high pressure component. For instance, the low pressure differential can be maintained across the tissue wall for a period of time that is about 5 minutes or less, about 2 minutes or less, or about 1 minute or less in some embodiments.

The high pressure differential can be established a single time or can be repeated over such time as desired until the tissue segment is essentially free of cells. The total decellularization time can vary, depending on the size and type of the tissue wall. By way of non-limiting example, the differential pressure process can be carried out cyclically for about 5 hours or more, about 10 hours or more or about 15 hours or more. In some embodiments, the differential pressure process can be carried out cyclically for about 20 days or less, or about 15 days or less, about 48 hours or less, or about 24 hours or less. In one embodiment, the fluids that contact the inner and outer surfaces of the tissue can be changed throughout a process. By way of example, a differential pressure can be established once or multiple times in a cyclic fashion with different treatment solutions applied in a sequential fashion over a complete course of treatment. Treatment solutions can include one or more decellularization solutions, sterilization solutions, fixation solutions, and so forth as generally known in the art and as discussed further herein. Following completion of the process, the decellularized tissue segment can contain about 5% or less by weight, about 3% or less by weight, or about 1% or less by weight of cells as compared to the amount of cells present in the pre-treated tissue segment.

A decellularization solution utilized in the process can be an aqueous solution that can include materials to encourage the decellularization process. For instance, the solution can include one or more biocompatible surfactants (e.g., anionic surfactants such as sodium dodecyl sulfate (SDS), nonionic surfactants such as Triton X100®, etc.), one or more detergents (e.g., sodium deoxycholate, sodium dodecyl sulfate, lithium dodecyl sulfate, sodium taurodeoxycholate, sodium taurocholate, sodium glycocholate, sodium cholate, sodium alkylbenzene sulfonate, N-lauroyl sarcosine, etc.), buffers (e.g., tris(hydroxymethyl)aminomethane (TRIS)), sodium hydroxide, scavengers such as ethylenediamine tetraacetic acid (EDTA), and so forth. Solution additives can generally be utilized in amounts as are generally known in the art, e.g., less than about 3% by weight.

The system can include additional components as needed. For instance, a system can include a pump, pulse dampeners (marked with "d" on FIG. 2), check valves and pressure transducers (marked with "p" on FIG. 2), heaters, etc. A pump can be, for example, a peristaltic pump or any other suitable pump that can deliver a solution at variable pressures according to a pulsatile pattern. The system can also include standard control systems. For instance, the pressure transducers, check valves, pulse dampeners, pump, etc. can be connected to programmable control systems (e.g., PLC's and the like) according to standard practices. By control of the system components, the pressure differential can be established and can be pulsed as described.

Figure 3:
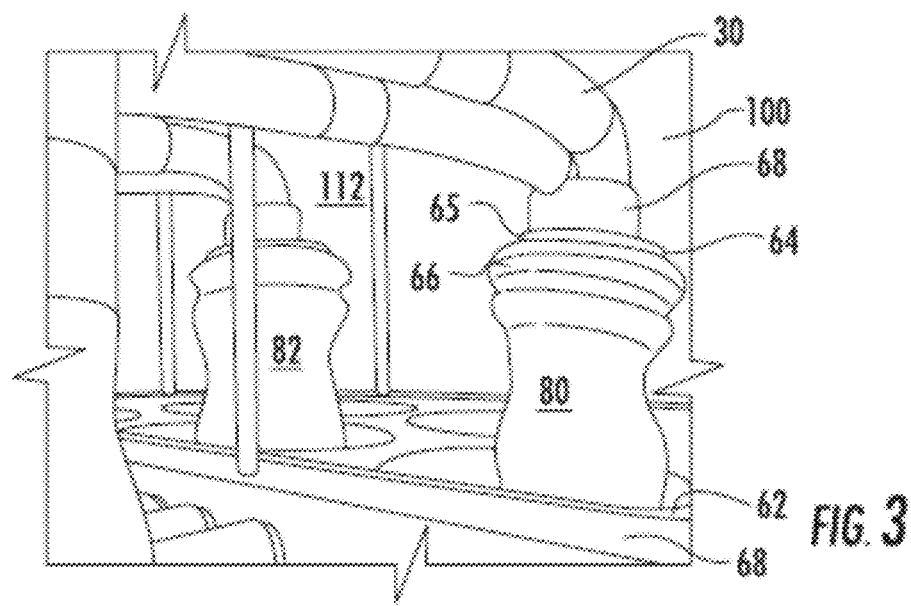
FIG. 3 illustrates two heart valves held in a multi-unit decellularization chamber.
Figure 4:
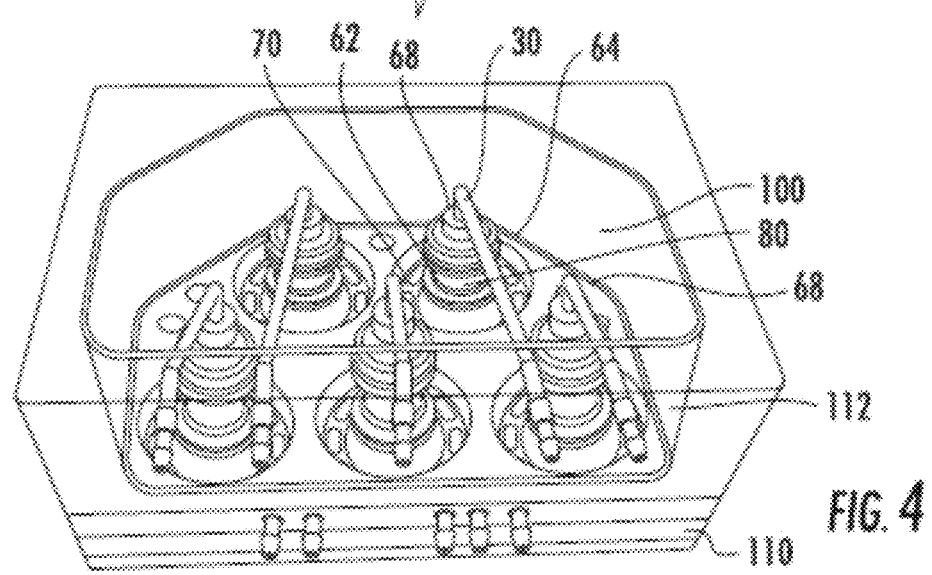
FIG. 4 illustrates a multi-unit decellularization chamber.

The tissue segment to be treated according to the disclosed method can be held with tissue holders that encourage the desired flow patterns and pressure differential. FIG. 3 and FIG. 4 illustrate a tissue segment 80 that is held at a first end by a first tissue holder 62 and held at a second end by a second tissue holder 64. Though illustrated in this embodiment as two different tissue holders, a tissue segment can be held with the same style of tissue holder at each end, if desired.

The tissue holder 64 is removably attachable to the tissue segment 80 so as to prevent leakage between the tissue wall 66 and the cap 65 of the tissue holder 64. The tissue holder 64 also includes an access port 68. The access port 68 can be attached to a flow line 30 via any suitable coupling. During use, the decellularization solution can flow through the lumen of the tissue segment 80, out of the port 68 and through the flow line 30.

Other tissue holders can be utilized in the system. For instance, the tissue holder 62 that is holding one end of the tissue segment 80 in FIG. 3 and FIG. 4 is a self-adjusting tissue holder. Briefly, the self-adjusting tissue holder 62 includes a first plate (not visible in FIG. 3) and a second plate 70 that are aligned with one another and hold a portion of the tissue segment therebetween. The self-adjusting tissue holder 62 also includes a clamping mechanism that, when tightened can press against the first or second plate. A spring (not visible in FIG. 3) can maintain pressure against the portion of the tissue segment held between the two plates. Upon decellularization, the tissue segment wall will lose mass and can become thinner. The tissue holder can be manually tightened to adjust to the mass loss as the tissue is decellularized. In one embodiment, the tissue holder can be a self-adjusting holder and can include the spring that can apply pressure to one of the plates. In this embodiment, the clamping force on the tissue can be maintained as the tissue is decellularized due to the spring included in the device that can maintain suitable force against the tissue held in the device and prevent leakage around the tissue segment or release of the tissue segment from the tissue holder 62.

The tissue segment 80 pictured in FIG. 3 is a heart valve tissue segment that can include the vessel wall and sinus, which can be seen in FIG. 3 as well as a valve, the cusps of which are within the lumen of the tissue segment 80 and not visible. The heart valve segment 80 can also include muscle tissue, which may be on the external portion of the segment and/or may be on the internal tissue wall. Those components of the tissue segment that are on the internal or external surface of the wall will not be subjected to the pressure differential. These segments will, however, still be decellularized through contact with the decellularization solution during the process much as they would in a standard immersion decellularization process.

As can be seen in FIG. 3, this particular tissue segment is an aortic root that includes coronary arteries that originate from the sinus of the segment. During a decellularization process, the coronary arteries can be ligated so as to maintain the pressure differential and the desired flow through the lumen of the segment.

The tissue segment 80 connected to the tissue holders 62, 64 has been located within a decellularization chamber 100 in FIG. 3 and FIG. 4. As can be seen, the flow line 30 passes through the wall of the decellularization chamber to carry the decellularization fluid (and optionally other treatment fluid) that has passed through the lumen of the tissue segment 80 out of the chamber 100.

The tissue holder 62 is seated in a tray 68 as shown. The tray 68 separates two sections of the decellularization chamber 100 from one another. The lower section 110 can be in fluid communication with a decellularization solution source that can pump the solution into the lumen of the tissue segment 80 from the end held by tissue holder 62. The fluid can then pass through the lumen and out of the flow line 30 that is in fluid communication with the end of the tissue segment 80 that is held by the tissue holder 64. A second flow line 35 can deliver a second flow of decellularization fluid into the upper section 112 of the decellularization chamber 100 where it can contact the external surface of the tissue segment 80. By control of the fluid parameters, a pressure differential can be established across the wall of the tissue segment 80. Following this period of pressure differential, the pressure of the higher pressure fluid (generally the flow through the lumen of the tissue segment) can be dropped until there is no or little pressure differential across the wall.

Figure 5:
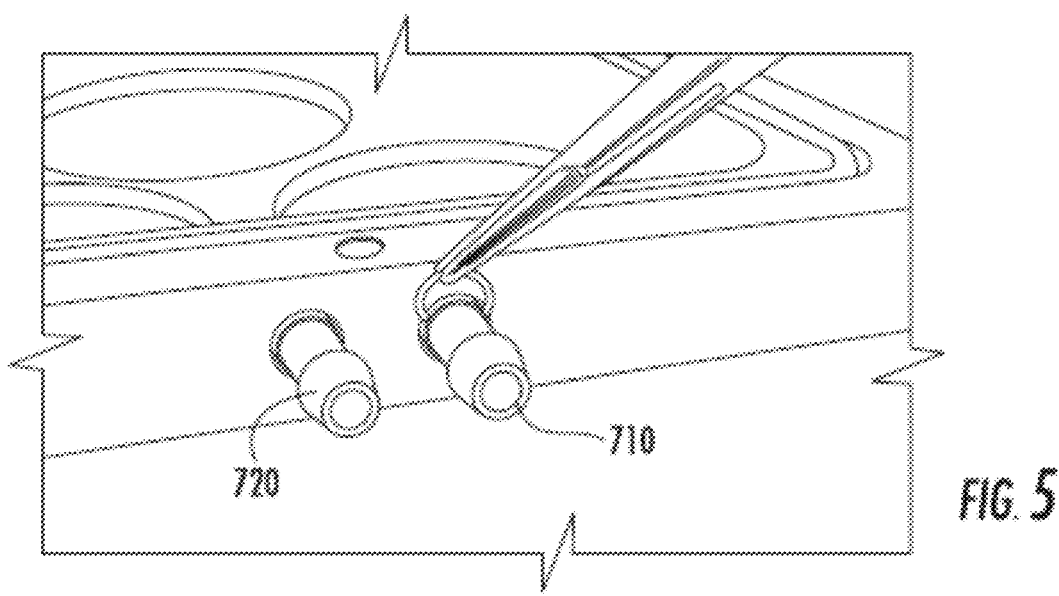
FIG. 5 illustrates access ports for a multi-unit decellularization chamber.

A decellularization system can be designed to decellularize multiple tissue segments at one time. For instance, FIG. 3 illustrates a decellularization chamber 100 that is carrying two tissue segments 80, 82. FIG. 4 illustrates that decellularization chamber 100 can hold five tissue segments for decellularization. In FIG. 5 can be seen access ports 710, 720 that can carry a decellularization solution into or out of the chamber. For instance, access ports 710, 720 can be connected to flow lines to carry the decellularization solution at high pressure into first section of the decellularization chamber. From there, the decellularization solution can pass into the lumen of the tissue segment held in the chamber.

Figure 6:
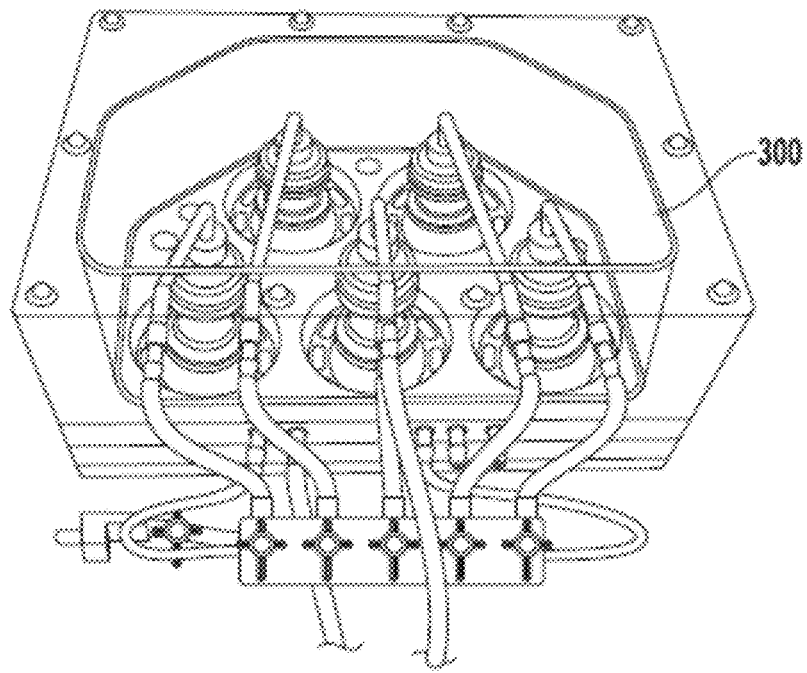
FIG. 6 is a top view of a multi-unit decellularization chamber.
Figure 7:
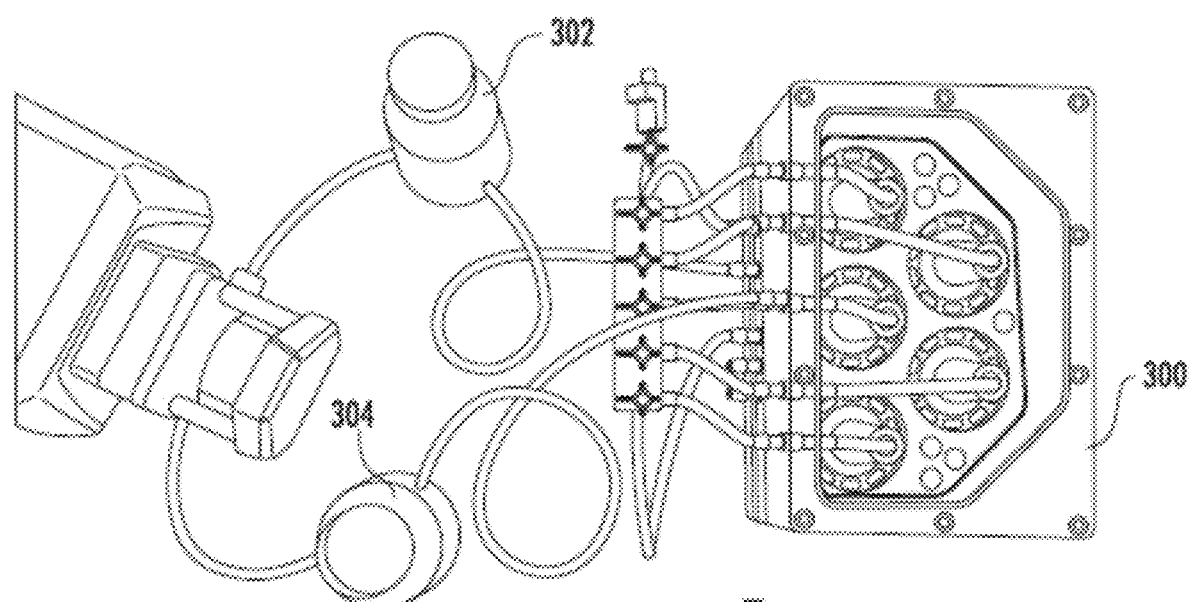
FIG. 7 is a top view of a multi-unit decellularization system.

FIG. 6 and FIG. 7 present additional views of the decellularization chamber 300 and external system components including reservoirs 302, 304 for the decellularization solution, flow lines, pump, etc. In one embodiment, the system can also include a warmer that can warm the decellularization solution(s).

A decellularization process can be carried out in conjunction with other tissue treatments as are known in the art. For instance, the structural protein components of the tissue can be fixed prior to, during, or following the decellularization process. A fixation process can be carried out, for instance, by perfusion of a fixative solution through the decellularization chamber so as to contact the interior and exterior surfaces of the tissue segment and crosslink or otherwise fix the structural components of the tissue. Perfusion of the other solutions (e.g., a fixation solution, a sterilization solution, etc.) can be carried out with a differential pressure established across the tissue wall or optionally can be carried out with no pressure differential established across the tissue wall, and merely with contact established between the solution and the tissue. In one embodiment, an individual treatment step can be carried out with differential pressure across the tissue wall over a period of time and another period with no differential pressure across the tissue wall, e.g., a first differential pressure period and a second period of perfusion with no differential pressure across the wall.

By way of example, a treatment step can be carried out in which acetic acid is utilized to swell the collagen fibers of the tissue, which can form porosity within the tissue and create a porous structure.

The elastin component of the decellularized tissue can be fixed by use of a polyphenolic compound as described in U.S. Pat. No. 7,252,834, which is incorporated herein by reference. Suitable phenolic compounds can include phenolic groups bound to a hydrophobic core. The phenolic compounds can stabilize elastin proteins through both steric means and bond formation and thereby protect sites on the protein susceptible to enzyme-mediated (e.g., elastase or MMP-mediated) cleavage. For instance, hydroxyl groups of a phenolic compound can bind elastin multivalently via hydrogen bond formation with amino acid residues including methionine, glycine and proline residues. As such, multiple proteins can interact with a single polyphenolic molecule to create a three-dimensional cross-link structure involving multiple elastin molecules. Moreover, the phenolic compound can include one or more double bonds that can covalently bind to the elastin, forming an even stronger and more permanent protective association between the phenolic compound and the elastin of the tissue segment. In addition, the large hydrophobic regions of the elastin protein can contain sites of association between the hydrophobic core of the phenolic compound and the protein. Thus, the association between the phenolic compound and the protein molecules can protect specific binding sites on the protein targeted by enzymes through the association of the protein with the hydrophobic core and can also sterically hinder the degradation of the protein through the development of the large three-dimensional cross-link structure.

Phenolic compounds can include synthetic and natural phenolic compounds. Natural phenolic compounds can include those found in extracts from natural plant-based sources such as extracts of olive oil (e.g., hydroxytyrosol (3,4-dihydroxyphenylethanol) and oleuropein; extracts of cocoa bean that can contain epicatechin and analogous compounds; extracts of *Camellia* including *C. senensis* (green tea) and *C. assaimic*; extracts of licorice; sea whip; aloe vera; chamomile; and the like.

Tannins including tannic acid and derivatives thereof can be utilized to fix the tissue segment. Tannic acid as a cross-linking agent is similar in many properties to that of many fixatives often used in the preparation and formation of xenograft or allograft tissue implants, for instance glutaraldehyde fixatives. As such, tannic acid can interact with other components of the decellularized tissue in addition to the elastin, and thus, can stabilize multiple components of the tissue segment. For instance, tannic acid is capable of cross-linking glycosaminoglycan polysaccharides as well as other connective tissue components.

To avoid toxicity, the phenolic compound can be high purity tannic acid, with little or no free gallic acid residue included in the compositions. For instance, a fixation composition can include less than about 5% free gallic acid residue in the preparation. In one particular embodiment the phenolic compound can be pentagalloylglucose (PGG). PGG includes the hydrophobic core of tannic acid, as well as multiple phenolic hydroxy groups but does not possess the outer gallic acid residues and the hydrolyzable ester bonds associated with tannic acid. Thus, the possibility of release of free gallic acid residues over the course of a long-term use can be prevented.

A tissue segment may be treated with other stabilization compounds as are known in the art, such as glutaraldehyde, which can crosslink and stabilize the collagen component of the decellularized tissue. Other treatment methods such as sterilization, recellularization, immersion decellularization, enzymatic removal of other non-structural and possible immunogenic components, can likewise be carried out prior to use of the decellularized tissue segment.

The present disclosure may be better understood with reference to the Example set forth below.

EXAMPLE

Fresh porcine aortic roots, which include the three aortic valve cusps, three sinuses, and a 2-3 inches long portion of the ascending aorta were collected together with surrounding adjacent tissues (thin endocardial wall segment and a portion of the mitral valve) from adult swine at a local abattoir and stored in ddH$_2$O on ice during transportation to the laboratory. The valve roots were macroscopically cleaned over ice by removing extraneous fat from the adventitial layer, cutting the aortic root to a length of about 2 inches and completely removing the sub-valvular fat, muscle, and mitral valve (for immersion decellularization) or thinning the sub-valvular fat and muscle to a thickness roughly equivalent to that of the mitral valve (for perfusion decellularization).

For immersion decellularization, the fresh aortic valve roots were decellularized using a ratio of 500 ml decellularization solution for 5 aortic roots. Briefly the procedure involved sequential treatment with ddH$_2$O, 0.05M NaOH, decellularization solution (0.05% SDS, 0.5% Triton X-100®, 0.5% sodium deoxycholate, and 0.2% EDTA in 10 mM TRIS), pH 7.5, 8 days at 22° C.) followed by nuclease treatment (DNAase+RNAase), 70% ethanol bioburden reduction and final 0.1% peracetic acid sterilization.

For perfusion decellularization, the fresh aortic valve roots were collected as described above and mounted onto a system as described herein at the level of the aortic root base by trapping a thin layer of cardiac muscle with endocardium intact and a layer of mitral valve tissue between two plastic rings secured in place by threaded stainless steel rings. The coronaries were ligated to direct all fluid through the valve. The system pressurized the interior of the valve root, thereby stretching portions of the root and sinus, driving fluids through the aortic wall while maintaining low pressure differential on the valve cusps. This subjected the cusps to immersion-like conditions while subjecting the sinuses and ascending aortas to a transmural pressure gradient of about 52±2 mmHg and cyclic mechanical stretching for 2.5 minutes on and 30 seconds off. After leaving the valve roots, the fluids were returned to the chamber so that roots would be concurrently bathed in circulating solutions. While in the decellularization device, the roots were subjected to the following conditions, with each step being followed by rinsing with water, ethanol, or 1×DPBS as appropriate:

1) hypotonic shock (ddH$_2$O, 24 hours, 22° C.);
2) loosening of the extracellular matrix and initialization of cell removal (0.1M NaOH, 2 hours, 22° C.);
3) detergent decellularization (1% sodium dodecyl sulfate, 1% Triton X-100, 1% sodium deoxycholate, and 0.2% EDTA in 50 mM TRIS, pH 7.5, 8 or 16 days at 22° C.);
4) enzymatic removal of nucleic acids (720 mU/mL DNase & 720 mU/mL RNAase in 5 mM MgCl$_2$ in PBS, 4 days at 37° C.);
5) sterilization (0.1% peracetic acid, 2 hours, 22° C.);
6) stabilization (0.15% pentagalloyl glucose, 20 hours, 22° C.) followed by a rapid glutaraldehyde fixation procedure.

The first four steps were carried out with cyclical differential pressure established across the tissue wall in a pulsatile fashion. The fifth step, sterilization, was carried out with differential pressure across the wall in a pulsatile fashion for the first hour and immersion contact with no differential pressure across the wall for the second hour. The final stabilization step was carried out without differential pressure across the wall, merely immersion on both sides of the tissue with the stabilization solutions.

Figure 8:
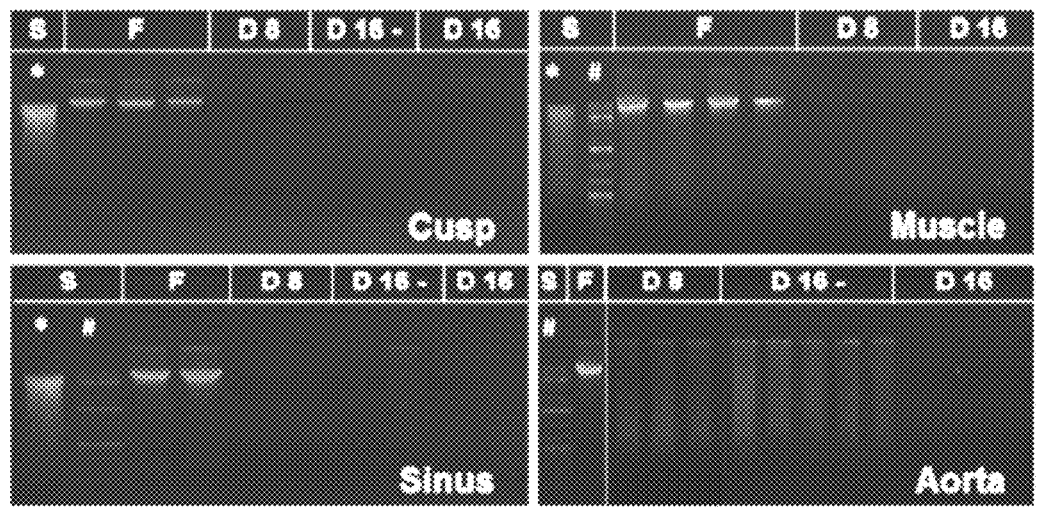
FIG. 8 illustrates the DNA content of different tissue areas of a heart valve prior to and following various decellularization protocols.

DNA was extracted from aorta, sinus, cusp and muscle tissue samples (n=4) and purified with the DNeasy Blood & Tissue Kit (Qiagen, Valencia, Calif.), then analyzed by Ethidium Bromide agarose gel electrophoresis. Samples were also quantified by reading absorbance at 260 nm on a NanoDrop machine. Quantities of DNA were normalized to dry tissue weight and expressed as ng/mg dry tissue. Results are shown in FIG. 8.

Figure 9:
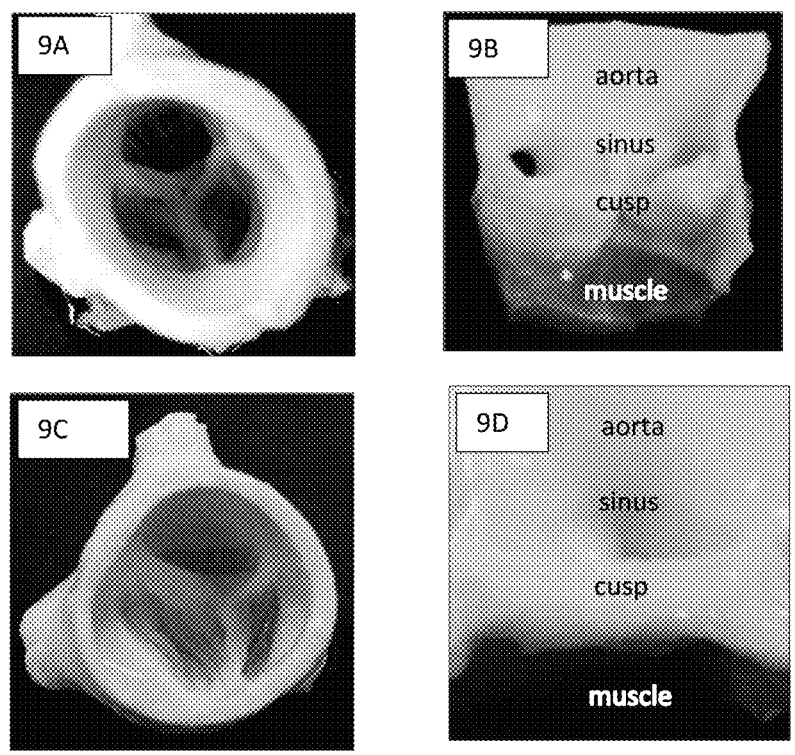
FIG. 9 illustrates a top view of a fresh aortic root and valve (FIG. 9A) and a fresh root and valve cut open with one cusp removed (FIG. 9B) and a fully decellularized root and valve in a top view (FIG. 9C) and cut open (FIG. 9D).

FIG. 9 presents images of a typical valve root prior to (FIG. 9A and FIG. 9B) and following (FIG. 9C and FIG. 9D) perfusions treatment. As can be seen, the walls of the valve root have lost mass due to the decellularization process.

For biaxial mechanical testing, samples were prepared from native (fresh) aortic valve leaflets and the decellularized aortic valve leaflets (N=6 for each group). Square-shaped samples (~12 mm×12 mm) were dissected from the belly region of the aortic valve leaflet, with one edge aligned with the leaflet circumferential direction and the other edge aligned with the leaflet radial direction. Thickness of each sample was measured in triplicate using digital calipers. Four dark markers were placed in the center region of the square sample (pasted on the ventricularis side of the leaflet). Samples were mounted onto the biaxial testing system via stainless steel hooks attached to 8 loops of 000 polyester suture of equal length (2 suture loops per sample edge). Membrane tensions (force/unit length) were applied to the circumferential direction and radial direction of the leaflet sample. A pre-load of 0.5 N/m was used during the biaxial mechanical testing. After 10 cycles preconditioning, the leaflet sample was loaded to an equi-biaxial tension of 60 N/m. The leaflet extensibility was characterized by the maximum stretch ratio along the circumferential direction ($\lambda$circ) and the maximum stretch ratio along the radial direction ($\lambda$rad). Biaxial testing was carried out with the samples submerged in in PBS bath (pH 7.4) at 37° C.

Bending tests carried out in a bath chamber with PBS. Aortic valve samples, both native and decellularized valve groups, were dissected out of the belly region of the valve leaflet (N=5 each group). These samples were further trimmed to tissue strips (~8 mm long by ~4 mm wide) in both the circumferential and radial directions. Two hollow posts (~4 mm) were attached to each end of the tissue strip for mounting purpose. One end of the tissue strips was attached to a post that was fixed on the inside wall of the bath chamber and the other end was mounted onto the bending bar. Each strip was mounted and subjected to simple bending testing with the ventricularis side up and the fibrosa side down. Five dark contrast markers used for tracking the leaflet strip curvature, i.e., marker 1 was pasted on the fixed post, marker 2 to 4 pasted along the edge of the tissue strip, and marker 5 pasted on the end of the bending bar. The bending movement was tracked using a Firewire camera (DMK21AF04 model, The Imaging Source).

Two different sizes of Titanium bending bars (grade 23, Small Parts Inc.), one with a diameter of 0.38 mm and the other with a diameter of 0.71 mm, were used for testing the native leaflets and the treated leaflets, respectively. Both bending bars had a length of 14 cm. The bending movement in the tissue strip was produced by moving the bath chamber toward the bending bar by a linear positioner controlled by a Velmex stepper motor (Velmex Inc., Bloomfield, N.Y.). The corresponding change in bending bar deflection was recorded by tracking marker pasted on the end of the bending bar, and the force was calculated by reference to the bending bar calibration curve. Both the Velmex motor and Firewire camera were controlled by a custom written Labview program (version 2000, National Instrument).

In addition to circumferential and radial directions, each leaflet strip was tested by flexing the strip with the natural curvature (WC) and against the natural curvature (AC). The WC tests result in the ventricularis layer being in tension and the fibrosa layer being in compression, while the AC tests result in the ventricularis layer being in compression and the fibrosa layer being in tension.

Results are represented as means±standard deviation in FIG. 10A, FIG. 10B, FIG. 11A, FIG. 11B, and FIG. 12. Statistical analysis was performed with one-way analysis of variances (ANOVA) and results were considered significantly different at $p<0.05$.

Figure 10A:
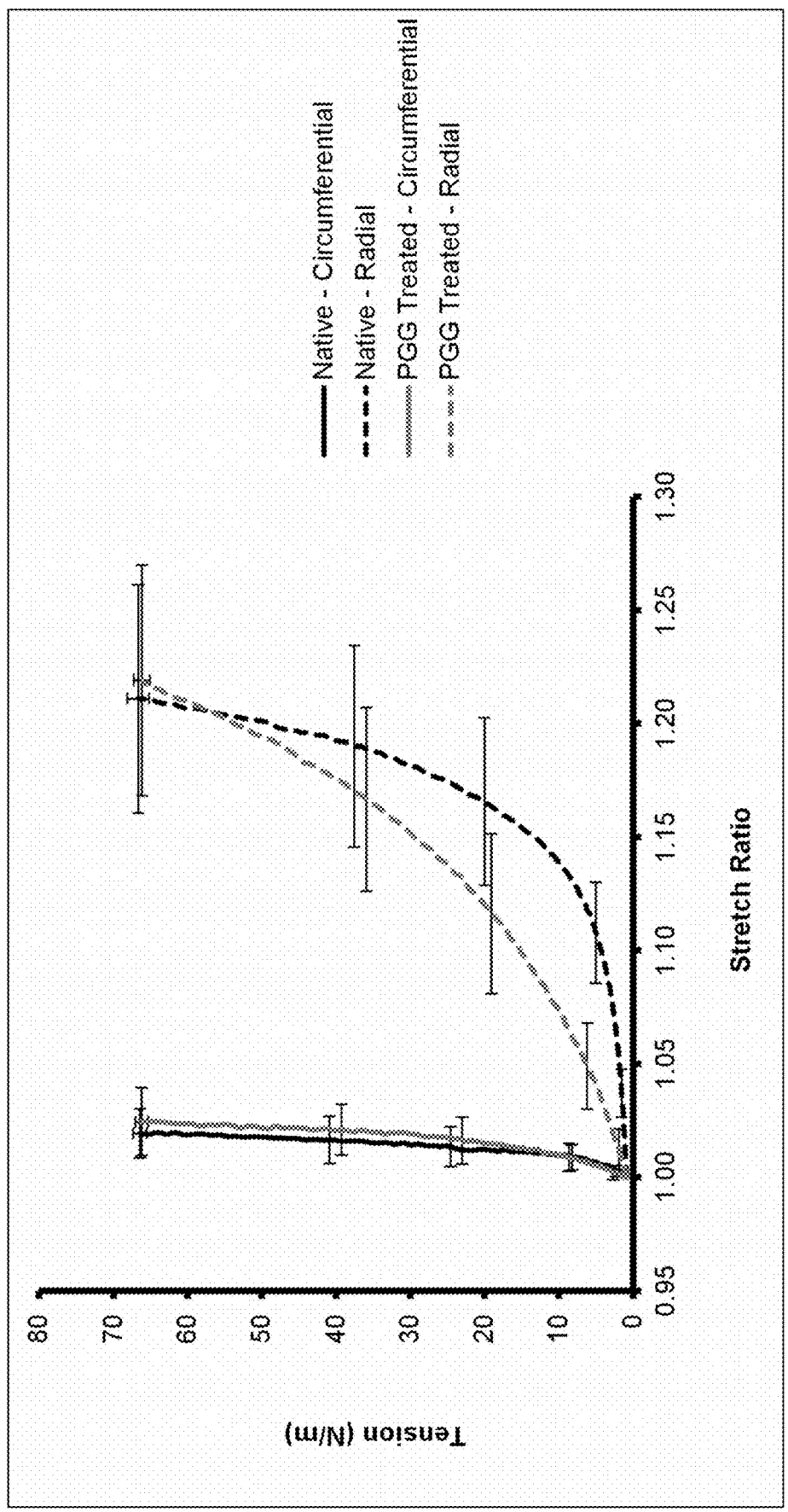
FIG. 10A graphically illustrates the biaxial stress-strain analysis of fresh valve cusps and cusps which underwent decellularization and PGG and glutaraldehyde stabilization, tested in both circumferential and radial directions.
Figure 10B:
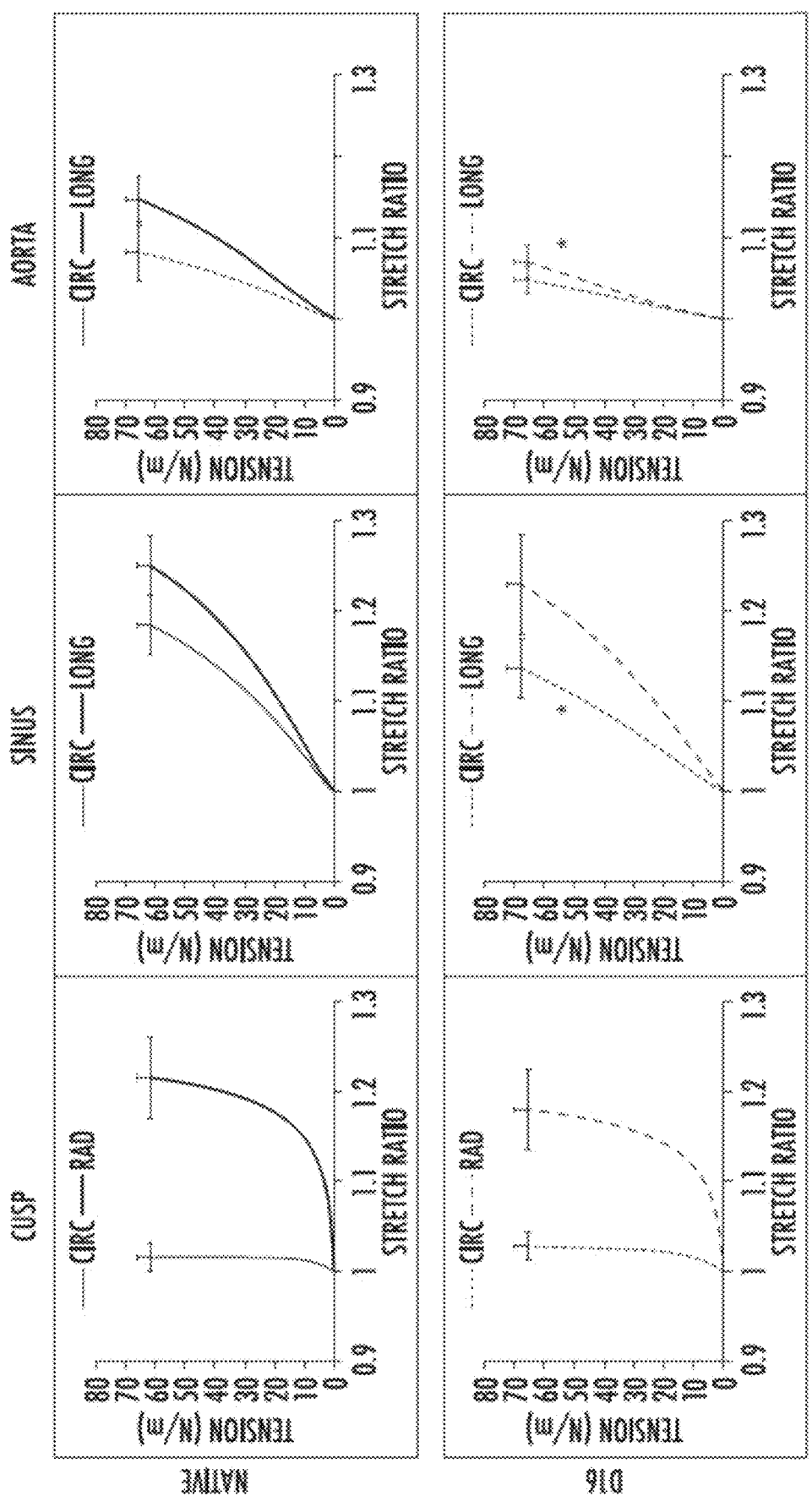
FIG. 10B graphically illustrates the mechanical properties of decellularized tissues and includes biaxial stress-strain analysis of aortic root tissue components before (native, top graphs) and after complete decellularization by 16 days perfusion (D16, lower graphs). Cusp tissues were tested in circumferential (Circ, darker lines) and radial axis (Rad, lighter lines) and sinus and aortic wall tissues in circumferential (Circ, darker lines) and longitudinal (Long, red lines) axis. * designates statistically significant differences in mean values of decellularized tissues as compared to native tissues for each testing axis.

The biaxial data obtained for both groups (native leaflets and 16 day treated leaflets) showed that the treated leaflets preserved the anisotropy of aortic valve leaflet tissue, i.e., a stiffer circumferential direction and more extensible radial direction (FIG. 10A). Moreover, the treatment protocol generated leaflet tissue with extensibility very close to the native leaflets. It was found that λcirc and λrad of the native leaflets were 1.0193±0.0108 and 1.2110±0.0504, respectively; and λcirc and λrad of the D16 treated leaflets were 1.0245±0.01507 and 1.2191±0.0509, respectively. However, it was noticed that the tension-stretch curve of the treated leaflets showed a much stiffer toe region in the radial direction when compared with the native leaflets (FIG. 10A).

The moment-curvature curves (FIG. 11A, FIG. 11B and FIG. 12) showed that AC bending was stiffer than the WC bending, and the circumferential direction bending is stiffer than radial direction. After the treatment, the aortic valve leaflets showed a large increase in overall bending stiffness. In treated leaflets, it was observed that AC bending was stiffer than WC bending, and circumferential was stiffer than radial. Moreover, the degree of nonlinearity increased after treatment, exhibiting a very stiff response when the bending curvature was small, but the increasing trend of the moment-curvature curve greatly slowed down after the bending curvature passed ~0.04 mm-1.

It is well known that for most decellularization protocols, the aortic valve leaflets experience an increase in overall tissue extensibility due to the microstructural disruptions (e.g., disruption of collagen network and elastin fibers). On the other hand, PGG treatment generates crosslinking at molecular level, which has a stiffening effect on collagenous tissues (see, e.g., U.S. Pat. No. 7,252,834, previously incorporated by reference). The treatment of PGG on the decellularized leaflets causes tissue crosslinking and stiffening, and hence, the extensibility of the decellularized leaflets could be reduced accordingly. Interestingly, the current decellularization protocol combined with the PGG and glutaraldehyde treatment generated leaflets with overall tissue extensibility comparable to the native leaflets. However, the biaxial behavior of the treated leaflets was not exactly the same as the native leaflets. The tension-stretch curves showed that the toe region of the radial direction is much stiffer than that of the native leaflets. The loss of a relatively flat toe region after treatment demonstrated that the treated leaflet picked up mechanical load much quicker in the deformation initiation region.

Figure 11A:
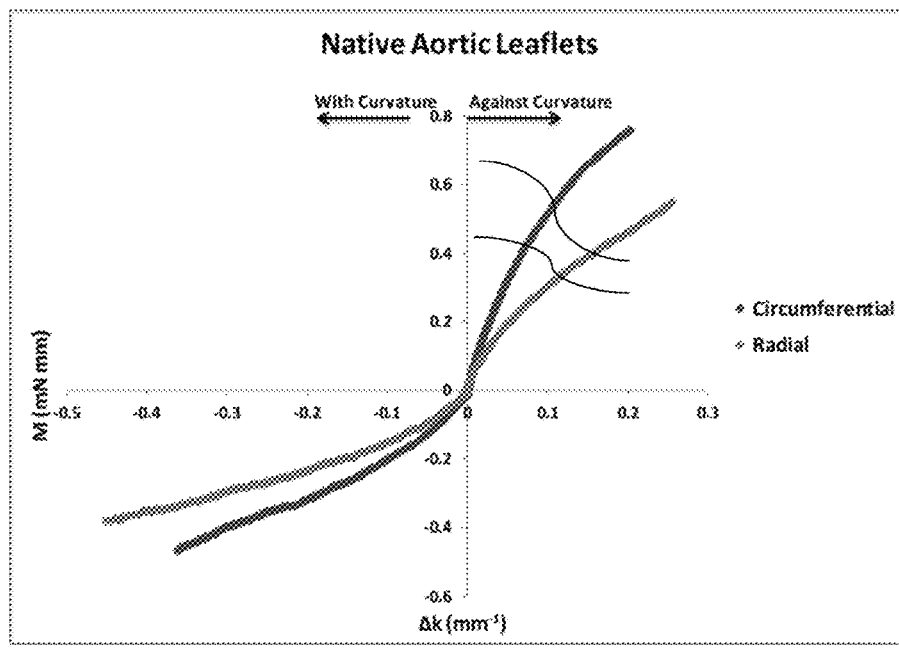
FIG. 11A graphically illustrates the bending test results for fresh cusps tested with curvature and against curvature.
Figure 11B:
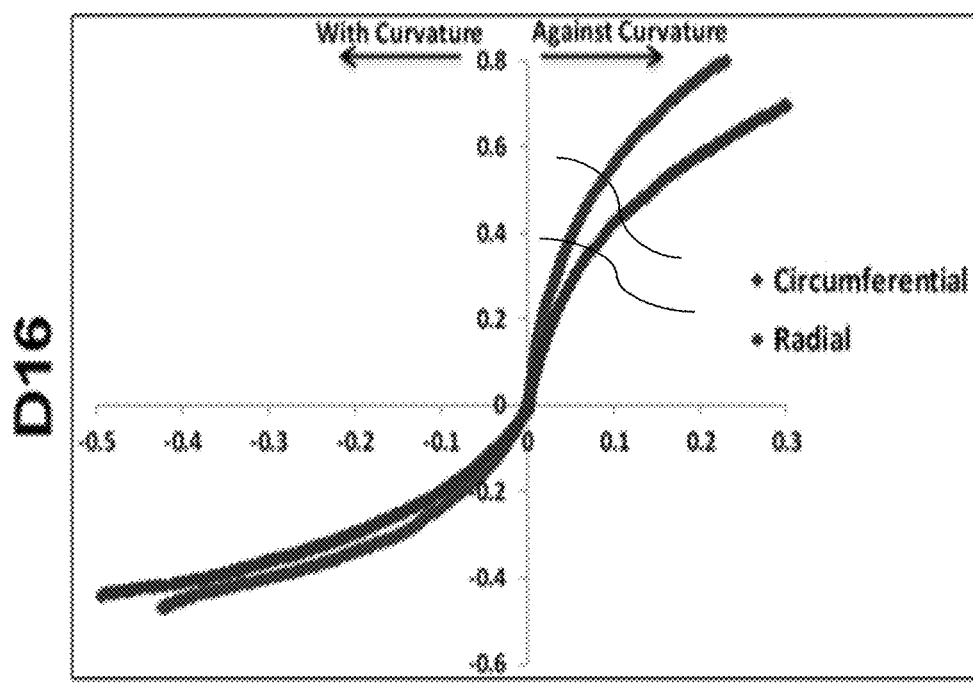
FIG. 11B graphically illustrates the bending test results for decellularized cusps tested with curvature and against curvature.
Figure 12:
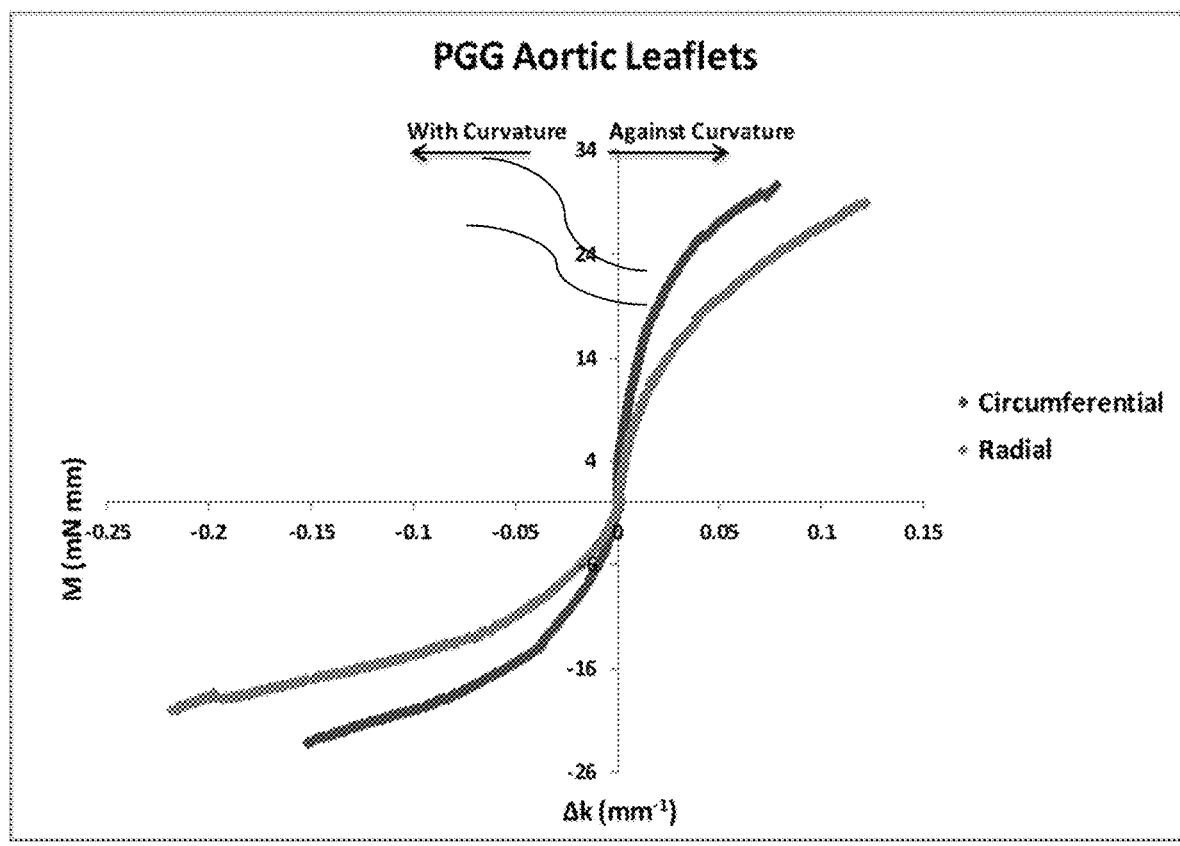
FIG. 12 graphically illustrates the bending test results for PGG-treated cusps tested with curvature and against curvature.

The treated aortic valve leaflets had a much stiffer bending moment-curvature relationship than the native aortic leaflets. This reflected the fact that crosslinking took place at the molecular level after PGG treatment. Tissue bending stiffness seemed to be more sensitive to this molecular level crosslinking, and the order of change observed was very high (FIG. 11A, FIG. 11B, FIG. 12). Interestingly, the subtle variations of leaflet flexure, in terms of AC vs. WC bending and circumferential vs. radial bending, were all preserved after PGG treatment. This observation implied that the PGG treatment still preserved the ultrastructural level subtlety while in overall increasing the tissue bending stiffness. The increase of the degree of nonlinearity after treatment was another interesting finding. As was noticed, the stiffening effect was more in the range of small bending curvature, and this observation echoed with the biaxial testing which showed the toe region of the radial direction curve turned into much stiffer after treatment.

Results comparing fresh and decellularized cusps showed that complete decellularization did not alter the natural anisotropy of root tissues. When comparing acellular cusps to native cusps, no statistically significant differences were found in biaxial mechanical properties (FIG. 10B) in either direction (p=0.623 for circumferential, p=0.330 for radial).

When tested for bending characteristics (FIG. 11A, 11B), the moment-curvature curves for both native and acellular cusps showed that against curvature bending was stiffer than with the curvature bending, and the circumferential direction bending was stiffer than the radial direction. Overall the decellularized cusps showed an almost identical trend in moment-curvature relationship to that of the native aortic valve cusps. The biaxial properties of the acellular sinus were also not statistically different from native sinus (p=0.7800 in the radial direction and marginally different in the circumferential direction, p=0.040). Conversely, the acellular aortic wall portion of the root was stiffer in the longitudinal direction (p=0.002) and not statistically different in the circumferential direction (p=0.220).

The decellularization protocol preserved the biaxial behavior of decellularized cusps. This is believed to be due to exposure of cusps to small differential pressures, low concentrations of detergents, and lack of protease treatments. When tested for bending, acellular cusps maintained moment-curvature trends comparable to that of native aortic valve cusps. The subtle variations of cusp flexure, when bended with and against curvature, in both circumferential and radial directions, were all preserved after the decellularization process. Taken together, these observations suggest that the decellularization process preserved the ultrastructural level subtleties of the aortic valve cusps.

The sinus and the aortic wall have a different structure and expectedly, effects of complete decellularization on the sinus and aortic wall were different when compared to the cusps. The most evident alteration was stiffening of the aortic wall when tested in the longitudinal direction. The mechanism of this process is unknown but it is hypothesized that this may be due to removal of components involved with stabilizing interactions between collagen fibers.

For histology studies, samples collected from the aortic wall, sinus, cusp and muscle were fixed in 10% formalin, embedded in paraffin, sectioned at 4-5 μm and stained with DAPI for nuclei, Hematoxylin & Eosin (H&E) and Movat's Pentachrome.

Figure 13:
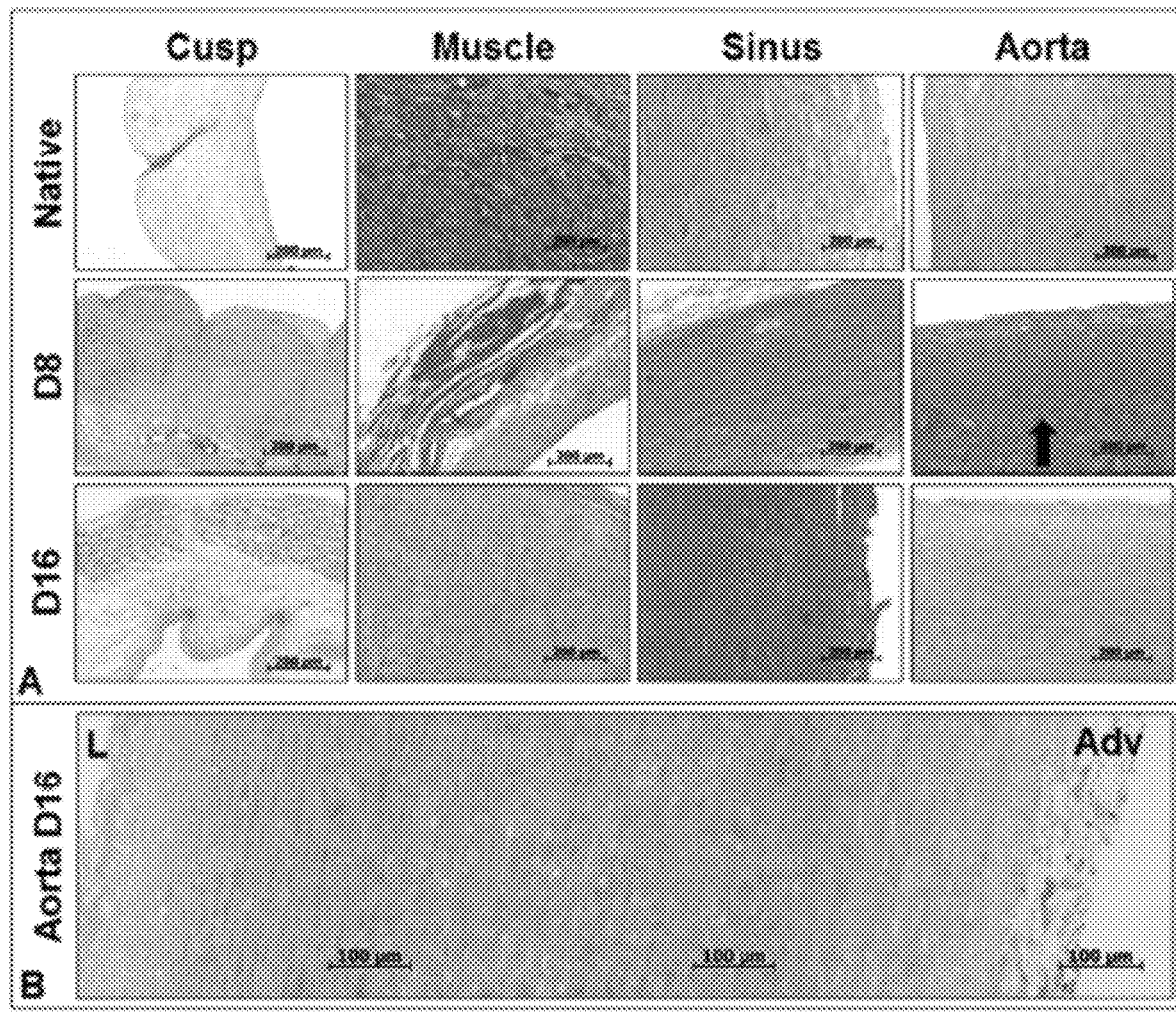
FIG. 13 illustrates hematoxylin and eosin (H&E) stained sections at A showing representative aortic root tissues before (Native) and after 8 days (D8) and 16 days (D16) of perfusion decellularization. Arrows point to stained cell nuclei remnants. H&E stain shows nuclei (darker) and cytoplasm and matrix (lighter). Representative panoramic composite of three images spanning the entire thickness of the acellular aortic wall (16 days perfusion) are shown at B. L, lumen; Adv, adventitia.

H&E staining (FIG. 13), which was adequate for assessment of overall tissue morphology, presence of cell nuclei, and visualization of the "pores" created by cell removal indicated that the aortic wall treated for 16 days was completely devoid of DAPI-stained nuclei. DNA analysis by EthBr agarose gel electrophoresis (FIG. 8) validated the histology data and showed that 16 days of perfusion decellularization followed by nuclease treatments were needed for complete DNA removal from the aortic wall. These results were also confirmed by NanoDrop quantification, showing a 10-fold reduction in DNA content after 16 days perfusion decellularization (data not shown).

Histology using DAPI nuclear staining showed that cusps, muscle and sinus tissues were readily decellularized by immersion or 8 days perfusion, as noted by disappearance of DAPI stained nuclei from tissue sections. However, the wall component of the root contained large numbers of cell nuclei in the middle ⅓ of the media in both immersion and 8-day perfusion treated roots, indicating restricted diffusion through the thick, dense, elastin-rich tissue. The aortic wall treated for 16 days was completely devoid of DAPI-stained nuclei. These results were confirmed by H&E staining (FIG. 13), which was adequate for assessment of overall tissue morphology, presence of cell nuclei, and visualization of the "pores" created by cell removal. DNA analysis by EthBr agarose gel electrophoresis (FIG. 8) validated the histology data and showed that 16 days of perfusion decellularization followed by nuclease treatments were needed for complete DNA removal from the aortic wall. These results were also confirmed by NanoDrop quantification, showing a 10-fold reduction in DNA content after 16 days perfusion decellularization (data not shown).

Figure 14:
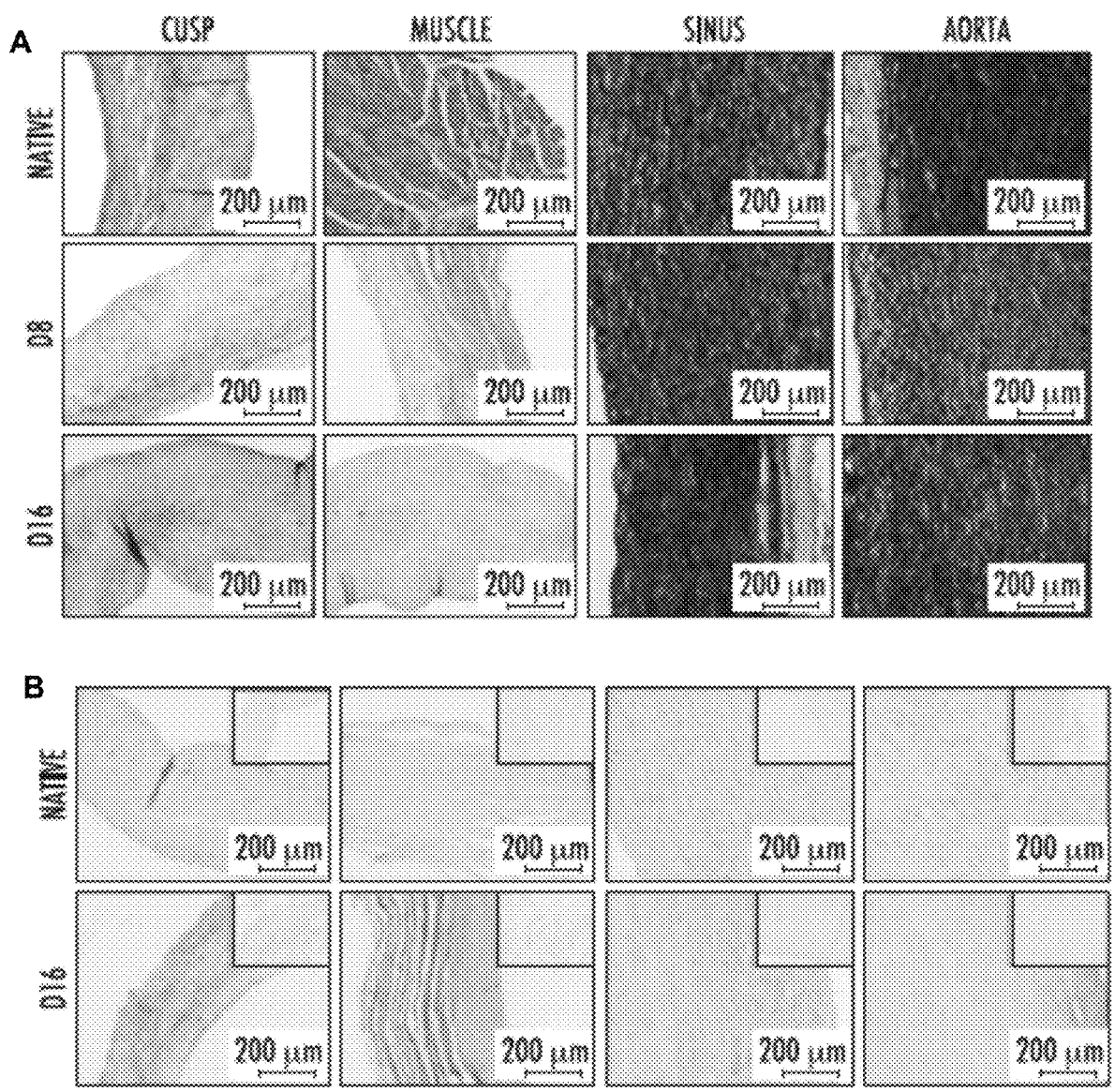
FIG. 14 presents representative Movat's pentachrome stained sections at A that reveals collagen, elastin and muscle cells in native aortic root tissues before (Native) and after 8 days (D8) and 16 days (D16) of perfusion decellularization. At B is presented representative images depicting immunohistochemical (IHC) staining for type IV collagen (positive IHC reaction; nuclei) in native aortic root tissues before (Native) and after 16 days (D16) of perfusion decellularization. Inserts illustrate the negative IHC controls.

Movat's Pentachrome staining performed on all tissues' components (FIG. 14) revealed preservation of intact extracellular matrix primarily comprised of collagen and elastin, without any visible changes in tissue structure after complete decellularization. Glycosaminoglycans (light blue on Movat's stain) were present in all native tissues but could not be detected in any tissues after decellularization. IHC staining revealed preservation of type IV collagen component of the basement membranes in all fully decellularized tissues.

Completeness of cell removal must be evaluated by several complementary methods which focus on localizing cell nuclei, cell remnants, and DNA. Thus, we defined fully acellular tissues, as those that corroborated complete lack of nuclei staining on H&E sections, lack of DAPI nuclei staining (which detects intact double stranded DNA), and minimal content of DNA as evidenced by EthBr agarose gel electrophoresis of extracted and purified genomic DNA. A more than 95% reduction in DNA content (corresponding to <50 ng/mg dry tissue) was considered a satisfactory threshold. Additional quantification by UV spectrophotometry (NanoDrop) has not always proven reliable, possibly because this method is not very sensitive at very low concentrations. To simplify data presentation, since immersion treatment was shown early on to be ineffective on the wall, the remainder of the results and analyses were focused only on the 8- or 16-days perfusion groups.

Integrity of the extracellular matrix is the second criterion important in development of acellular tissue scaffolds. This was evaluated on histological sections using Movat's pentachrome and IHC. Overall, the 16-day perfusion method preserved the main matrix components (collagen, elastin, type IV collagen) in all segments of the root, with the exception of GAGs, which were lost during decellularization. GAGs are lost very easily during tissue preparation steps which utilize aqueous solvents. It is not known what effects the paucity of GAGs would have on the durability of implanted acellular scaffolds; certainly, this aspect requires more investigation.

Figure 15:
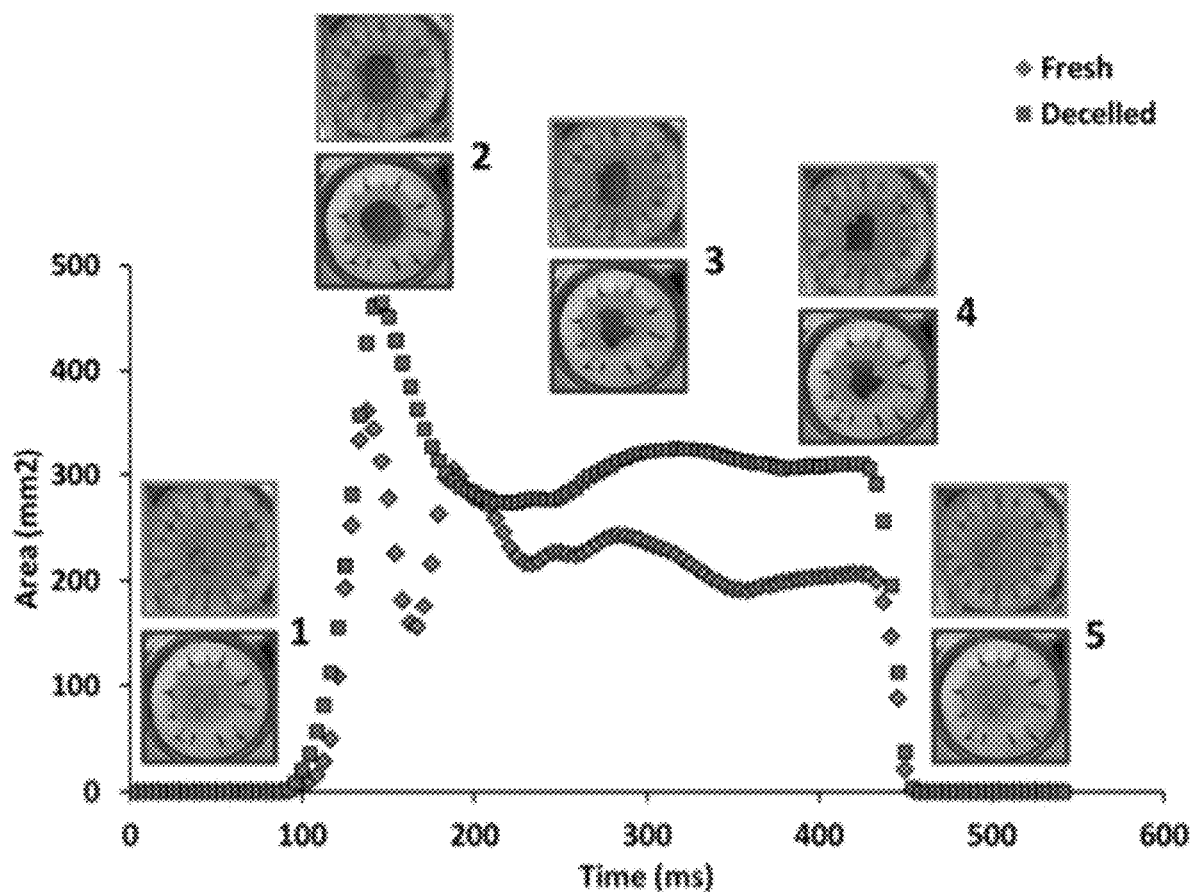
FIG. 15 illustrates Hemodynamics of acellular aortic roots. Average geometric orifice areas (in mm2), normalized to valve diameter as a function of time (means for n=3 cycles per valve) are shown for fresh (diamond) and 16-day perfusion decellularized (square) aortic roots. Representative images (top of each pair, fresh roots; bottom of each pair, decellularized roots) are shown as inserts for the closed position (1), fully open (2), midway through the open phase (3), just before starting to close (4), and fully closed again (5).

Whole roots were tested under a variety of conditions in the heart valve bioreactor (FIG. 15). The valves functioned well at aortic parameters of flow and pressures without regurgitation and their functionality did not change with time over multiple cycles. Maximum GOAs reached about 400-470 mm2 for the 22-24 mm diameter roots. During each cycle, both the native and acellular roots opened quickly (in cca. 50 ms) with well-coordinated cusp motions. While in the fully open segment, slight movement of the sinuses and apparent fluttering of the cusps was recorded for several hundreds of milliseconds. The valves remained open for about 300 ms after which they closed rapidly, within less than 20 ms, without regurgitation.

The roots were mounted onto the purpose-designed supports and tested under a variety of conditions. Notably, both acellular and native valves opened and closed under very low pressures (not shown) indicating that the decellularization protocol did not change the cusp tissue response to minute changes in pressures and flow. Overall, the acellular valve roots functioned well, and their functionality did not change with time over multiple cycles. The GOA for acellular valve roots was within acceptable limits for valves of 22-24 mm diameters.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A method for decellularizing a tissue segment, the tissue segment including a lumen and a tissue wall surrounding the lumen, the tissue wall having an interior surface facing the lumen and an exterior surface that is opposite the interior surface, the method comprising:
    contacting the interior surface of the tissue wall with a decellularization solution as the decellularization solution passes through the lumen;
    pumping the decellularization solution out of the lumen of the tissue segment and into a first flow line;
    pumping the decellularization solution out of the first flow line and into a second flow line that is in fluid communication with and downstream of the first flow line;
    contacting the exterior surface of the tissue wall with the decellularization solution after the decellularization solution exits the second flow line; wherein the decellularization solution follows a flow path that sequentially exits the lumen of the tissue segment, passes through the first flow line, passes through the second flow line, and enters a decellularization chamber within which the tissue segment is retained to contact the exterior surface of the tissue wall;
    establishing a pressure differential across the tissue wall from the interior surface to the exterior surface for a period of time of about 1 minute or more, the pressure differential being from about 15 mmHg to about 150 mmHg; and
    following the period of time, decreasing the pressure differential to a lower pressure differential across the tissue wall, the lower pressure differential being about 15 mmHg or less.

2. The method of claim 1, further comprising circulating the decellularization solution along the flow path and thereby repeating the method of claim 1 one or more times.

3. The method of claim 2, wherein the decellularization solution is circulated for a period of time of about 5 hours or longer.

4. The method of claim 2, wherein the decellularization solution is circulated for a period of time of about 20 days or less.

5. The method of claim 1, wherein the period of time is about 5 minutes or less.

6. The method of claim 1, wherein the lower pressure differential comprises no pressure differential.

7. The method of claim 1, wherein the tissue segment is a vascular segment.

8. The method of claim 1, wherein the tissue segment comprises a heart valve in the lumen.

9. The method of claim 1, wherein the tissue segment comprises muscle tissue.

10. The method of claim 1, wherein the tissue segment comprises an aortic root.

11. The method of claim 1, wherein following the decrease in the pressure differential, the tissue segment is held at the lower pressure differential for a period of time following which the method of claim 1 is repeated.

12. The method of claim 1, wherein following the decrease in the pressure differential, the tissue segment is held at the lower pressure differential for a period of time following which the method of claim 1 is repeated with a second, different decellularization solution.

13. The method of claim 1, further comprising fixing the tissue segment.

14. The method of claim 13, wherein the tissue segment is fixed by use of a polyphenolic compound.

15. The method of claim 1, further comprising heating the decellularization solution.

16. The method of claim 15, wherein the first decellularization solution is heated to a temperature of about 37° C.

* * * * *